United States Patent [19]
Backman et al.

[11] Patent Number: 5,792,607
[45] Date of Patent: *Aug. 11, 1998

[54] METHOD AND KITS FOR AMPLIFYING TARGET NUCLEIC ACIDS APPLICABLE TO BOTH POLYMERASE AND LIGASE CHAIN REACTIONS

[75] Inventors: Keith C. Backman, Bedford, Mass.; Sheila B. Bond, Lake Forest, Ill.; John J. Carrino, Gurnee, Ill.; Thomas G. Laffler, Libertyville, Ill.

[73] Assignee: Abbott Laboratories, Abbott Park, Ill.

[*] Notice: The term of this patent shall not extend beyond the expiration date of Pat. Nos. 5,427,930 and 5,573,907.

[21] Appl. No.: 412,023

[22] Filed: Mar. 28, 1995

Related U.S. Application Data

[63] Continuation of Ser. No. 634,771, Jan. 9, 1991, abandoned, which is a continuation-in-part of Ser. No. 470,674, Jan. 26, 1990, abandoned.

[51] Int. Cl.$^6$ .................... C12Q 1/68; C12P 19/34
[52] U.S. Cl. .................... 435/6; 435/91.1; 435/91.2; 435/810; 436/501; 536/23.1; 536/24.1; 536/24.3; 536/24.31; 536/24.32; 536/24.33; 935/77; 935/78; 935/88
[58] Field of Search .................... 435/6, 91.1, 91.2, 435/810; 436/501; 536/22.1, 23.1, 24.1, 24.3; 935/77, 78, 88

[56] References Cited

U.S. PATENT DOCUMENTS

| | | | |
|---|---|---|---|
| 4,689,405 | 8/1987 | Frank et al. | 536/27 |
| 4,851,331 | 7/1989 | Vary et al. | 35/6 |
| 5,185,243 | 2/1993 | Ullman et al. | 435/6 |
| 5,427,930 | 6/1995 | Birkenmeyer et al. | 435/91.52 |

FOREIGN PATENT DOCUMENTS

| | | |
|---|---|---|
| 201 183 A3 | 3/1986 | European Pat. Off. |
| 0246864 | 11/1987 | European Pat. Off. |
| 0320308 | 6/1989 | European Pat. Off. |
| 357 336 A2 | 8/1989 | European Pat. Off. |
| WO 89/10415 | 11/1989 | WIPO |
| WO 90/12115 | 10/1990 | WIPO |

OTHER PUBLICATIONS

Nickerson et al, Automated DNA diagnostics using an ELISA-based oligonucleotide ligation assay, *Proc. Natl. Acad. Sci. USA*, 87:8923–8927 (1990).

Sikwek et al., The relative importance of *Escherichia coli* exonuclease III and endonuclease IV for the hydrolysis of 3'-phosphoglycolate ends in polydeoxynucleotides, *Nucl. Acids Res.*, 16(11):5031–5038 (1988).

Bailly and Verly, The multiple activities of *Escherichia coli* endonuclease IV and the extreme lability of 5'-terminal base-free deoxyribose 5-phosphates, *Biochem. J.* 259:761–768 (1989).

Levin et al, Homogeneous *Escherichia coli* Endonuclease IV. *J. Biol. Chem.*, 263(17):8066–8071 (1988).

Doetsch & Cunningham, The enzymology of apurinic/apyrimidinic endonucleases, *Mutation Research*, 236:173–201 (1990).

Wu et al., *Genomics* 4, (1989), pp. 560–569.

Brutlag et al., J. Biol. Chem., vol. 247, No. 1, Jan. 10, 1972, pp. 241–248.

(List continued on next page.)

*Primary Examiner*—Ardin H. Marschel
*Attorney, Agent, or Firm*—Thomas D. Brainard; Paul D. Yasger

[57] ABSTRACT

The present invention involves methods of improving LCR and PCR amplification schemes by modifying at least one probe/primer end so that the probability of the probe/primer contributing to spurious signal development is greatly reduced. Only after specific hybridization of the modified probe/primer with true target, are the modified ends "corrected" in a target dependent fashion to allow participation of the probe/primer in the enzymatic assembly reaction. Specific modifications depend on whether the assembly is done by ligation (as in LCR) or by extension/elongation (as in PCR).

49 Claims, 3 Drawing Sheets

OTHER PUBLICATIONS

Au, et al., *Escherica coli* mutY Gene Encodes an Adenine Glucosylase Active on A Mispairs, *Proc. Natl. Acad. Sci. USA*, 86:8877–8881 (1989).

Lu, et al., A Novel Nucleotide Excision Repair of the Conversaion of an A/G Mismatchto C/G Base Pair in *E. coli*, *Cell*, 54:805–812 (1988).

Lu, et al., Specific A/G-to-C.G Mismatch Repair in *Salmonella typhimurium* LT2 Requires the mutB Gene Product, *J. Bacteriol*, 172:1232–1240 (1990).

Michaels, et al., MutY, an Adenine Glycosylase Active on G-A Mispairs, Has Homolog to Endonuclease III. *Nucl. Acids, Res.*, 18:3841–3845 (1990).

Hennecke, et al., The vsr Gene Product of *E. coli* K-12 is a Strand-and Sequence-Specific DNA Mismatch Endonuclease, *Nature*, 353:776–778 (1991).

Carrano et al, Genomics 4, 1989, pp. 129–136.

Ikehara, et al., Advances in Carbohydrate Chemistry and Biochemistry, vol. 36, "The Synthesis of Polynucleotides", 1979, pp. 135–213.

METHOD AND KITS FOR AMPLIFYING TARGET NUCLEIC ACIDS APPLICABLE TO BOTH POLYMERASE AND LIGASE CHAIN REACTIONS

This application is a continuation of U.S. pat. application Ser. No. 07/634,771 filed Jan. 9, 1991, now abandoned, which is a continuation-in-part of application Ser. No. 07/470,674, abandoned, entitled IMPROVED METHOD OF AMPLIFYING TARGET NUCLEIC ACIDS USING LIGASE CHAIN REACTION, filed Jan. 26, 1990, which enjoys common ownership and is incorporated herein by reference.

BACKGROUND

This invention relates to methods of amplifying target nucleic acids and, particularly, to methods of performing ligase or polymerase chain reaction amplifications wherein at least one of the probes or primers is reversibly modified at the reaction initiation site so that it is not a substrate for the enzyme catalyzed reaction. Exemplary modifications include chemical blockage of reactant groups, addition of one or more nucleic acid bases to form an "overhang", or absence of one or more nucleic acid bases to form a "recess". The modified end prevents or reduces target independent spurious signal development and is later corrected in a target dependent manner to enable amplification.

In many cases, the feasibility of a nucleic acid based diagnostic assay is dependent on the ability to amplify the signal generated by only a few molecules of target. Although signal amplification is one potential solution, target amplification is often the preferred solution in nucleic acid based assays. Target amplification involves the repeated copying or duplication of sections of the nucleic acid designated as the target.

In the target amplification technique known as polymerase chain reaction (PCR) a pair of primers (one primary and one secondary) is employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to increase geometrically the number of target sequence molecules. PCR is described further in U.S. Pat. Nos. 4,683,195 and 4,683,202.

An alternate mechanism for target amplification is known as ligase chain reaction (LCR). In LCR, two primary (first and second probes) and two secondary (third and fourth) probes are employed in excess. The first probe hybridizes to a first segment of the target strand and the second probe hybridizes to a second segment of the target strand, the first and second segments being contiguous so that the primary probes abut one another in 5' phosphate-3' hydroxyl relationship and so that a ligase can covalently fuse or ligate the two probes into a fused product. In addition, a third (secondary) probe can hybridize to the first probe and a fourth (secondary) probe can hybridize to the second probe in a similar abutting fashion. Of course, if the target is initially double stranded, the secondary probes will also hybridize to the target complement in the first instance. Once the fused strand of primary probes is separated from the target strand, it will hybridize with the third and fourth probes which can be ligated to form a complementary, secondary fused product. In order to understand LCR and the improvements described herein, it is important to realize that the fused products are functionally equivalent to either the target or its complement. By repeated cycles of hybridization and ligation, amplification of the target sequence is achieved. This technique is described more completely in EP-A-320 308, the entire disclosure of which is incorporated herein by reference.

One of the great strengths of amplification reactions is their ability to detect exceedingly small numbers of target molecules.

However, it is important that the amplification process be highly specific since the amplification of untargetted sequences along with signal could potentially impair the reliability of the amplification process. Both PCR and LCR are capable of generating and even amplifying non-specific or spurious background signal. Due to the different principles underlying PCR and LCR, sources of background signal are different for each, and will be discussed separately.

A potential problem associated with ligase chain reaction is background signal caused by target independent ligation of the probes. Since the third probe hybridizes to the first probe and the fourth probe hybridizes to the second probe, the probes, which are added in excess, can easily form duplexes among themselves. These duplexes can become ligated independently of the presence of target to form a fused product which is then indistinguishable from the desired amplified target, yet which is still capable of supporting further amplification. Although target independent blunt-end ligation of these duplexes is a relatively rare event, it is sufficiently common to cause undesirably high background signals in diagnostic assays.

A commonly recognized source of spurious background signal in PCR is the hybridization of a primer sequence to regions of the DNA molecule not intentended to be amplified. Generally these hybridizations occur because the target sample contains, in addition to the target sequence itself, other sequences with some similarity to the target sequence. Although hybridization of primer to these similar sequences is not as probable as to the target sequence, some hybridization can occur. When such unintended non-specific hybridization occurs, if the 3' terminal nucleotide of the primer molecule is sucessfully hybridized to a complementary nucleotide of the target molecule, it is possible that primer extension may be sucessfully initiated by the polymerase enzyme, leading to the generation of an oligonulceotide different than the target sequence. Under some circumstances, this nucleotide may even undergo exponential amplification. Whether amplified or not, the spurious nucleotide sequence may, under some analysis situations, be taken to be indicative of target sequence and thus lead to erroneous results.

SUMMARY OF THE INVENTION

Although oligonucleotide probes and primers serve dramatically different roles in LCR and PCR, respectively, the terms "initiator" and "probe/primer" are used herein where general discussions can apply to both. It is a primary object of the present invention to improve the sensitivity of nucleic acid based assays by decreasing the occurrence of spurious signal generation. This object is met in the present invention by modifying at least one probe/primer end so that the probability of the probe/primer contributing to spurious signal development is greatly reduced. Only after specific hybridization of the modified probe/primer with the target, are the modified ends "corrected" in a target dependent fashion to allow participation of the probe/primer in the enzymatic amplification reaction.

One feature of the invention, useful in either LCR or PCR, provides a nucleic acid probe/primer in which a chemical moiety blocks or masks a group which is obligatorily involved in the enzyme catalyzed step of the amplification reaction. This enzymatic step is ligation in LCR and extension or elongation in PCR. In either case, the probe/primer is capable of hybridizing with the target and initiates the enzymatic reaction (thus, the term "initiator") and the ligated or extended product is referred to as an "amplification product".) The blocking group is selected so that it can be removed by an enzyme substantially only when the probe/primers are hybridized to the target. In another aspect, a probe/primer is modified to contain an overhang of additional bases at one end. The bases are later cleaved in a target dependent fashion allowing the amplification reaction to occur.

According to another feature specific for LCR, the probes have recesses relative to the point of ligation which create a gap when hybridized to the target. The gap is then filled in a target dependent manner to render the probes ligatable. Gap filling can be accomplished by extension of one or more probes, or by the use of additional fifth and sixth probes followed by ligation.

Another object of the invention is to provide an improved method for distinguishing a first sequence from a second sequence, the first differing from the second by only a single base in the target region. The first sequence may be viewed as a target, and the second sequence may be viewed as a potentially cross reactive strand that can be distinguished.

Briefly, the invention relates to a method of amplifying a target nucleic acid sequence enzymatically, wherein an enzyme utilizes a nucleic acid probe/primer as an initiator; the target sequence to which it hybridizes as a template; and additional nucleosides (either strung together as oligonucleotides or individually as triphosphates, or both) as building blocks to enzymatically assemble amplification products complementary to the target, the amplification products themselves serving as further templates; wherein the improvement comprises:

(a) providing requisite initiators capable of hybridizing with the target, wherein at least one of the initiators is modified such that, when the initiator is hybridized, the enzyme is substantially incapable of recognizing the initiator as its substrate, so that amplification product is not assembled;

(b) hybridizing the initiator to the target, if present, to form an initiator-template complex;

(c) correcting the modification in a target dependent manner to render the initiator-template complex recognizable by the enzyme;

(d) enzymatically assembling an amplification product; and (e) dissociating the amplification product from the target and repeating the hybridization, correction and assembling steps to amplify the desired target sequence.

The correcting and assembling reagents are described in more detail below.

DETAILED DESCRIPTION

General Outline of the Detailed Description
I. LCR Modifications
  A. Overhanging Modified Ends
    1. Ribonucleotide modifications
    2. Abasic site cleavage
    3. Base Mismatch Repair
  B. Ends Modified by Recesses
    1. Gap Filling by Extension
    2. Gap Filling by Additional Probes
II. PCR Modifications
  A. Overhanging Modified Ends
  B. Ends Modified by Recesses (not applicable)

For purposes of this invention, the target sequence is described to be single stranded. However, this should be understood to include the case where the target is actually double stranded but is simply separated from its complement prior to hybridization with the probes/primers. In the case of double stranded target, secondary probe(s) (For LCR, the third and fourth probes, A' and B'; for PCR, the additional primer, B) will also participate in the initial step by hybridizing to the target complement. In the case of single stranded target, the secondary probes or primers will not participate in the initial hybridization step, but will participate in subsequent hybridization steps. Target sequences may comprise deoxyribonucleic acid (DNA) or ribonucleic acid (RNA).

Throughout this application, the "prime" (') designation is used to indicate a complementary base or sequence. A probe or primer is "complementary" to another sequence if it hybridizes to the sequence and has substantially complementary base pairs in the hybridized region. Thus, probe A can be complementary to A' even though it may have ends not coterminal with A'. The same is true of B and B'. Similarly, the short sequences $X_n$ and $Y_m$ have complementary sequences designated as $X'_n$ and $Y'_m$, respectively. Finally, the complement of a single base, e.g. Q, is is designated as Q'. As used herein with respect to sequences, "complementary" encompasses sequences that have mismatched base pairs in the hybridizable region, provided they can be made to hybridize under assay conditions.

It is also to be understood that the term "the 4 bases" shall refer to Guanine (G), Cytosine (C), Adenine (A) and Thymine (T) when the context is that of DNA; but shall refer to Guanine (G), Cytosine (C), Adenine (A) and Uracil (U) in the context of RNA. The term also includes analogs and derivatives of the bases named above. Although the degenerate base Inosine (I) may be employed with this invention, it is not preferred to use I within modified portions of the probes according to the invention.

I. LCR

Figure 2A:
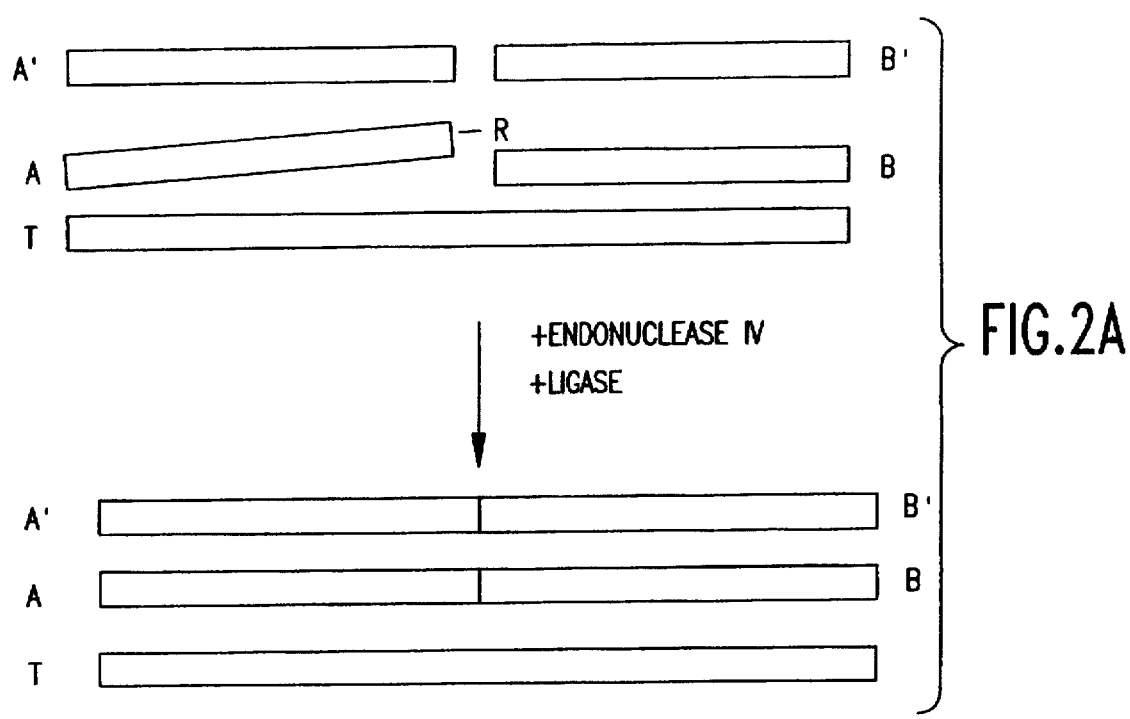
FIGS. 2A and B are graphic representations of the overhang embodiment, wherein R represents a blocking moiety and "rBrBrB" represents a ribonucleotide extension.
Figure 2B:
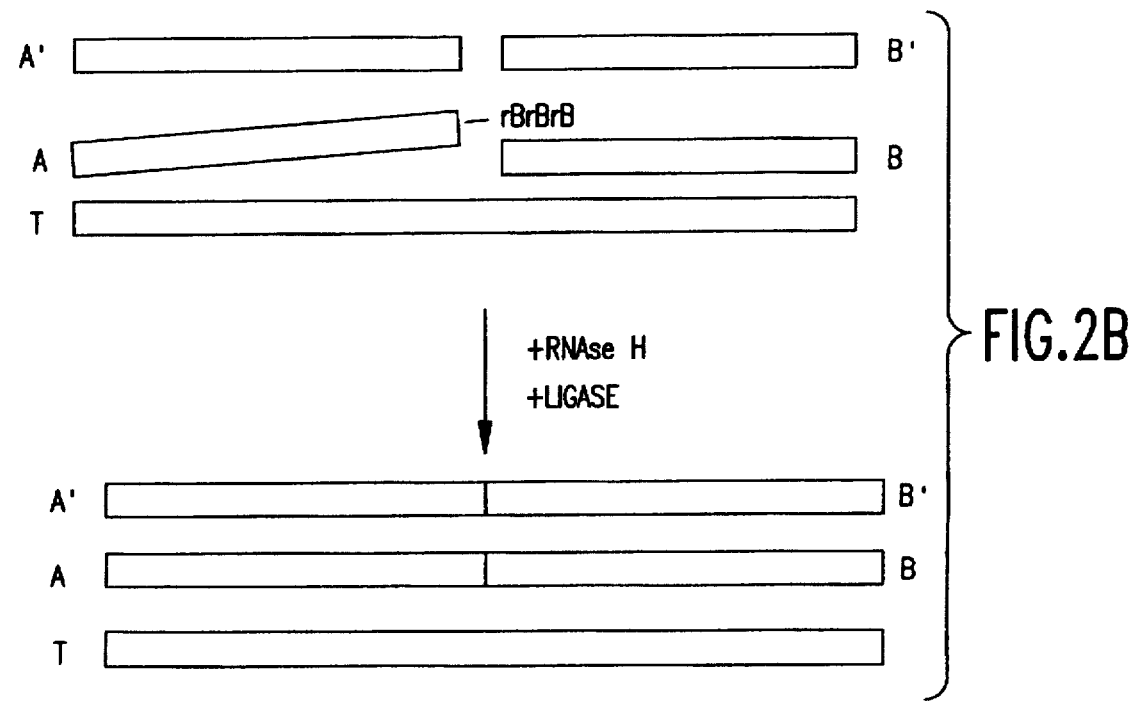

With regard to LCR, it is an important feature of the present invention that instead of using two pairs of probes capable of forming blunt-ended duplexes, at least one probe of one of the probe pairs initially includes a "modified" end which renders the resultant duplex "nonblunt" and/or not a suitable substrate for the ligase catalyzed fusion of the two probe duplexes. A "modified end" is defined with respect to the point of ligation rather than with respect to its complementary probe. A "modified end" has either (1) a blocking moiety (or additional base residues) on a group (e.g. the 5' phosphate or the 3' hydroxyl) which, under ordinary LCR conditions, obligatorily participates in the ligase catalyzed fusion (See e.g. probe A of FIGS. 2A and 2B); or (2) omitted bases to create a "gap" between one probe terminus and the next probe terminus (See e.g. probe B of FIG. 3; probes A' and B, of FIG. 4; and probes D and E of FIG. 5.)

By convention in this application, a modified end of the first type is referred to as an "overhang", the overhang being an additional blocking moiety or additional base residues which, when hybridized to the target sequence extends beyond the point of ligation. The term "overhang" is not to be confused with an extension of one probe with respect to its complementary probe, resulting from the fact that they need not be coterminal. A modified end of the second type is referred to herein as a "recess", the recess being the gap between two primary or secondary probes after hybridizing to the target. The presence of these modified ends reduces the falsely positive signal created by blunt-end ligation of complementary probe duplexes to one another in the absence of target.

"Correction" of the modification is subsequently carried out to render the probes ligatable. As used herein "correction" refers to the process of rendering, in a target dependent manner, the two primary probes or the two secondary probes ligatable to their partners. Thus, only those probes hybridized to target, target complement or polynucleotide sequences generated therefrom are "corrected." "Correction" can be accomplished by several procedures, depending on the type of modified end used.

As used herein, "point of ligation" or "intended point of ligation" refers to a specific location between two probe partners that are to be ligated in a template-dependent manner. It is the site at which the "corrected" probe lies adjacent its partner in 5' phosphate-3' hydroxyl relationship. For each set of four LCR probes there are two "points of ligation", a point for the primary probe partners and a point for the secondary probe partners. In conventional LCR the two points of ligation are opposite one another, thus forming blunt ended duplexes when the probe pairs hybridize to one another. In the present invention, the points of ligation may be opposite one another only in the "overhang" embodiments. They are displaced from one another in the "recess" embodiments by one or more bases by virtue of the gaps. The exact point(s) of ligation varies depending on the embodiment and, thus, this term is further defined in the context of each embodiment.

Each of the probes may comprise deoxyribonucleic acid (DNA) or ribonucleic acid (RNA). It is a routine matter to synthesize the desired probes using conventional nucleotide phosphoramidite chemistry and the instruments available from Applied Biosystems, Inc. (Foster City, Calif.); DuPont, (Wilmington, Del.); or Milligen, (Bedford, Mass.). Phosphorylation of the 5' ends of the probes, while necessary for ligation by ligase, may be accomplished by a kinase, as is known in the art.

Throughout this application, the bases X, Y and Q, and their complements are described as being selected from certain subsets (N or M) of the 4 bases. In reality, the sequences are not "selected" at all, but are dictated by the sequence of the target strand. The term "selected" in this context is taken to mean that a target sequence having the desired characteristics is located and probes are constructed around an appropriate segment(s) of the target sequence.

In general, the methods of the invention comprise repeated steps of (a) hybridizing the modified probes to the target (and, if double stranded so that target complement is present, to the target complement); (b) correcting the modification in a target dependent manner to render the probes ligatable; (c) ligating the corrected probe to its partner to form a fused or ligated product; and (d) dissociating the fused product from the target and repeating the hybridization, correction and ligation steps to amplify the desired target sequence. Steps (a), (c) and (d) are essentially the same for all of the embodiments and can be discussed together. They are generally the same steps that one would employ in conventional LCR. Step (b) varies depending on the type of modification employed and each different type is discussed separately.

Hybridization of modified probes to target (and optionally to target complement) is adequately explained in the prior art; e.g EP-320 308. Probe length, probe concentration and stringency of conditions all affect the degree and rate at which hybridization will occur. Preferably, the probes are sufficiently long to provide the desired specificity; i.e, to avoid being hybridizable to random sequences in the sample. Typically, probes on the order of 15 to 100 bases serve this purpose. Presently preferred are probes having a length of from about 15 to about 40 bases.

The probes are added in approximately equimolar concentration since they are expected to react stoichiometrically. Each probe is present in a concentration ranging from about 5 nanomolar (nM) to about 90 nM; preferably from about 10 nM to about 30 nM. The optimum quantity of probe used for each reaction also varies depending on the number of cycles which must be performed. Optimum concentrations can readily be determined by one of ordinary skill in this art The stringency of conditions is generally known to those in the art to be dependant on temperature, solvent and other parameters. Perhaps the most easily controlled of these parameters is temperature and thus it is generally the stringency parameter varied in the performance of LCR. Since the stringency conditions required for practicing this invention are not unlike those of ordinary LCR, further detail is deemed unnecessary, the routine practitioner being guided by the examples which follow.

The next step in the general method follows the specific correction step and comprises the ligation of one probe to its adjacent partner. Thus, each primary probe is ligated to its associated primary probe and each secondary probe is ligated to its associated secondary probe. An "adjacent" probe is either one of two probes hybridizable with the target in a contiguous orientation, one of which lies with its phosphorylated 5' end in abutment with the 3' hydroxyl end of the partner probe. "Adjacent" probes are created upon correction of the modified end(s) in a target dependent manner. Since enzymatic ligation is the preferred method of covalently attaching two adjacent probes, the term "ligation" will be used throughout the application. However, "ligation" is a general term and is to be understood to include any method of covalently attaching two probes. One alternative to enzymatic ligation is photo-ligation as described in EP-A-324 616.

The conditions and reagents which make possible the preferred enzymatic ligation step are generally known to those of ordinary skill in the art and are disclosed in the references mentioned in background. Ligating reagents useful in the present invention include prokaryotic ligases such as *E coli* ligase, T4 ligase and *Thermus thermophilus* ligase (e.g., ATCC 27634) as taught in EP-320 308. This latter ligase is presently preferred for its ability to maintain activity during the thermal cycling of LCR. Absent a thermally stable ligase, the ligase must be added again each time the cycle is repeated. Also useful are eukaryotic ligases, including DNA ligase of Drosophilia, reported by Rabin, et al., *J. Biol. Chem.* 261:10637–10647 (1986).

Once ligated, the fused probe is dissociated (e.g. melted) from the target and, as with conventional LCR, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation are not free themselves to participate in other unwanted ligation reactions. Thus, ligatable sticky or blunt ends should be avoided. If such ends must be used, then free 5' terminal phosphates should be avoided or eliminated. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below.

Following amplification, the amplified sequences can be detected by a number of conventional ways known in the art. In a particularly preferred way, hooks are attached at the available outside ends of at least two probes (opposite ends of fused product), and preferably to the outside ends of all four probes. A "hook" is any moiety having a specific ligand-receptor affinity. Typically, the hook(s) at one end of the fused product (e.g. the 5' end of A and the 3' end of A') comprises an antigen or hapten capable of being immobilized by a reagent (such as antibody or avidin) coated onto a solid phase. The hook(s) at the other end (e.g. the 3' end of B and the 5' end of B') contains a different antigen or hapten capable of being recognized by a label or a label system such as an antibody-enzyme conjugate. Exemplary hooks include biotin, fluorescein and digoxin among many others known in the art. A substrate is then added which is converted by the enzyme to a detectable product. EP-A-330 221 to Enzo describes oligonucleotides having a biotin molecule attached at one end.

A. OVERHANGING MODIFIED ENDS

As mentioned, a first embodiment involves a modified end wherein a blocking moiety or additional bases are added to at least one probe beyond the point of intended ligation. The blocking moiety or the additional bases comprise the "overhang" and are the reason blunt-end ligation is not possible. In a first variation, the overhang comprises a chemical blocking agent, R.

It is well known that the standard DNA ligase reaction requires that the substrate strands present a 3' hydroxyl and a 5' phosphate at the point of ligation. Several modifications, particularly at the 3' hydroxyl group, are known to introduce an R group which will render the modified end incapable of participating in a ligase reaction, but which can be removed when the modified strand is part of a double stranded structure. Such modifications include the following illustrative R groups attached to the 3' hydroxyl oxygen in place of the hydrogen atom:

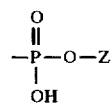

wherein Z is selected from the group consisting of —H;— $(CH_2)_n$ CHO, where n is from 1 to about 3, preferably 1 or 2;,-deoxyribose; and -dideoxyribose.

The synthesis of probes having ends suitably modified with an R group is well known in the art. For example, chemical synthesis of oligonucleotides containing a 3' phosphate group has been described by Markiewicz and Wyrzykiewicz, *Nucl. Acids Res.* 17:7149–7158 (1989.). Larger blocking groups, which may have the advantage of hiding the 3' phosphate from non-specific phosphatases that might be present in some samples, are conveniently prepared by creating the oligonucleotide probe with terminal transferase and dUTP or ddUTP, followed by treatment with uracil glycosylase. Purification of uracil glycosylase is taught by Lindahl, et al. *J. B. C.* 252: 3286–3294 (1977). In the case of dUTP addition, treatment with strong base following the uracil glycosylase treatment can be used to prepare the glycoaldehyde derivative. It is to be understood that the examples of R groups given above are illustrative only, and that one of ordinary skill could synthesize many variants which would work equally well.

The enzyme endonuclease IV (Siwek, et al. *Nucl. Acids Res.* 16:5031–5038 (1988)) will remove such blocking groups and expose a 3' hydroxyl group if and substantially only if the strand containing the blocking group is hybridized to a complementary strand. Although target independent correction of the modified ends due to activity of endonuclease IV on the AA' or BB' duplexes is rare, if necessary, it can be further minimized by designing the probes complementary to those with modified ends, such that they are recessed by one or more nucleotides.

In another variation of overhanging ends, the overhang consists of additional nucleic acid bases which can be cleaved off once the probes are hybridized to target. The overhang prevents ligation by virtue of its bulk at the intended point of ligation, and stereochemically blocks or masks the group(s) which obligatorily participate in the ligase reaction (as described for blocked ends). What distinguishes this from the simple chemical blockage described above is the nature and size of the "blocking" group (i.e., the overhang). It is by nature composed of nucleic acid residues colinear with the probe molecule. However, the size of the group is too large to permit the modified end of the molecule to remain in the vicinity of the ligation point when hybridized to a target. Moreover, since the overhang is to be removed, it may Jbe designed so that it cannot participate in a ligase catalyzed reaction at all (e.g., by lacking a 5' phosphate group).

Three classes of overhangs are described, though the selection is meant to be illustrative only. Those skilled in the art will appreciate that other enzymes capable of similarly removing overhangs may be used in completely analogous ways. Exemplary cases are:

1. an overhang consisting essentially of ribonucleotides (when the target consists of DNA);
2. an overhang containing an abasic site; and
3. an overhang containing a base which results in a mismatched base pair with a base in the target.

In general, however, the overhang must be complementary to the target so that its removal can be template dependent as is described below. The overhang may be from 1-10 bases, preferably from 1-5 bases in length.

1. Ribonucleotide modifications.

Synthesis of DNA oligonucleotides containing ribonucleotides has been described by Atabekov, et al. *FEBS Let* 232:96–98 (1988). DNA probes having modified ends consisting of ribonucleotide residue extensions can be used in this invention. The ribonucleotides fail to present a proper substrate for ligase and the modified probes will not be ligated or amplified. In principle these extensions may be either at the 5' or 3'end of a selected probe.

"Correction" is by removal of ribonucleotides. Enzymes generally called ribonuclease H are known to be widely distributed in nature. One such ribonuclease H is available from Sigma Chemicals (Cat# $R_{6501}$). Such enzymes selectively remove ribonucleotides from nucleic acid strands in which they are present if and substantially only if that strand is hybridized to a strand of DNA. Although there is some debate as to whether a particular ribonuclease (RNAse) removes all or only all but one ribonucleotide from a strand, that need not concern us in general, since at least some ligases (e.g. T4 ligase) are known to be capable of ligating ribonucleotides to deoxyribonucleotides. For any particular RNAse H, it is simple enough to determine for purposes of LCR whether it leaves zero or one ribonucleotide residue. One merely makes two ribomodified LCR probe sets, designed on the basis that the enzyme removes either all or all but one of the ribonucleotides, and determines the performance of the LCR reaction in each case. Once established, the enzyme behavior can thereafter be taken as a given. In practice, different RNAse H species may be more or less facile at correcting a 3' or a 5' modification. This is readily determined empirically for any given RNAse H species.

Such ribonucleotide modified probes are used in an LCR reaction. When two probe partners hybridize to adjacent regions on the target, they cannot be joined by ligase unless and until RNAse H "corrects",—i.e. removes the ribonucleotides from —the modified probe. In the case where the ribonucleotides are at the 5' end of the probe, an internal phosphate group is exposed to serve as a substrate in the ligase reaction. This obviates the need for a special step in the manufacture of the probe to add such a 5' phosphate.

Upon ligation, the fused probes function as a new target, just as in standard LCR.

2. Abasic site cleavage.

A variety of widely distributed enzymes (e.g., endonuclease IV; Siwek, et. al., supra) cleave a single strand of DNA at the location of an abasic site substantially only when the DNA strand is in duplex form hybridized to its complement. The synthesis of oligonucleotides with abasic sites has been described in the art by Takeshita, et al, *J. B. C.* 262:10171–10179 (1987). Modified oligonucleotide probes can be synthesized so as to position an abasic site immediately 5' to the point of ligation on the probe intended to donate its 5' end, or immediately 3' to the point of ligation on the probe intended to donate its 3' end. In either case, the complementary probe should be designed so that when hybridized together the two probes would not allow target independent cleavage at the abasic site by the enzyme to be used. The probe set could be designed with short offsets of the two points of ligation so that no double stranded structure would occur in the immediate vicinity of the abasic site except when the probe was hybridized to true target. In this way, correction is target dependent.

In the case of hybridization to target, cleavage at the abasic site would expose an end capable (by both its position and its chemical nature) of being joined by ligase to an adjacent probe. Upon ligation, the fused molecule functions as a new target, as in standard LCR.

3. Mismatch Repair.

Perhaps the easiest of all "modified" oligonucleotides are those which contain no unusual features whatsoever outside of the context of the hybridized state. Such oligonucleotides can be readily prepared by standard synthetic techniques using standard commercial reagents. When hybridized to a target, however, the unique modification of such probes manifests itself: a mismatched base pair is present in the duplex. There are many biological systems known which can correct or repair such mismatched base pairs. Although any such system may in principle be adapted to correcting the modification in a LCR probe set, we will discuss one system in further depth as an illustration of a general approach.

An enzyme (or complex of enzymes) has been reported by an et al. *Proc. Natl. Acad. Sci. USA.* 86:8877–8881 (1989), which can specifically recognize mismatches of A opposite G. In such "A/G mismatches", the enzyme cleaves the strand containing the A between the A and the next residue in the chain. Thus, probes can be designed in which the overhang is separated from the remainder of the probe by an A residue, and that A residue occurs in a position that falls opposite a G residue when the probe is hybridized to a true target. Upon hybridization to a true target, the overhang is cleaved from the remainder of the probe, including the mismatched A residue, exposing an end which, by virtue of its position and chemical nature, is capable of being joined by ligase to another probe positioned adjacently. Upon ligation, the resulting fused molecule can serve as a target in subsequent rounds of LCR.

As a further feature, such schemes can be used to determine the identity of a specific base locus which may exhibit allelism. In the specific AG mismatch example, for instance, about five sixths of such changes can be directly assayed. The initial identity of a specific locus must either be A, T, G, or C. If it is G, then a mutant is other than G; similarly if it is C, its complement is G and the complement of the mutant is not G. If, it is A or T, then two thirds of such mutants are either G or C. Thus one half of single base mutant alleles result in the loss of a specific G, and two thirds of the remainder result in the appearance of a specific G residue. In either case, a strategically placed A residue in one of the members of an LCR probe set can strongly influence the rate of appearance of fused probe molecules. In the case of the loss of a G residue, the A containing probe will fail to be cleaved and the progress of the LCR reaction will be severely impaired. In the case of the appearance of a new G, cleavage of an A containing probe is enabled and the rate of LCR reaction is greatly enhanced. Those skilled in the art will readily appreciate that other mismatch repair systems with differing specificities might readily be adapted to identify other single base changes at specific loci in a manner analogous to the described AG mismatch repair system.

B. ENDS MODIFIED BY RECESSES

In a second embodiment, modified ends are created by eliminating from one or more of the probes a short sequence of bases, thereby leaving a recess or gap between the 5' end of one probe and the 3' end of the other probe when they are both hybridized to the target (or target complement, or polynucleotide generated therefrom). In order for LCR to amplify the target, the gaps between the probes must be filled in (i.e., the modification must be "corrected"). In a first version, this can be done using a polymerase or a reverse transcriptase and an excess of deoxynucleotide triphosphates which are complementary to the target strand opposite the gap. Alternatively, this can be done by supplying a fifth probe complementary to the target and a sixth probe complementary to the fifth probe. These alternative versions are separately described below.

However, prior to discussing this embodiment in detail, a brief digression on set terminology may be helpful. A set (e.g., S) consists of all the elements contained within the set S. The set "not S" then consists of all the remaining elements of the "Universe" which are not found in S. The "Universe" for purposes of this application consists of the four bases G, C, A and T, or G, C, A and U as described above. The intersection of set S and another set (e.g., R) consists only of those elements which are found in both S and R. Thus, as used in this application, the set "not N and not M" consists of those bases which are present in neither the gap $X_n$ nor the gap $Y_m$. According to this invention, the set "not N and not M" must not be an empty set; i.e at least one base must remain in this set to code for the "stopbase".

1. Gap Filling by Extension:

In accordance with this first version, the invention involves repeated steps of (a) hybridizing the probes to the target (and, if double stranded so that target complement is present, to the target complement); (b) extending at least one probe to fill in at least one gap, designated $X_n$; (c) ligating the extended probe to the adjacent probe to form a fused or ligated product; and (d) dissociating the fused product from the target and repeating the hybridization, extension and ligation steps to amplify the desired target sequence.

In this version, the "gaps" $X_n$ which impart the "modified ends" are "corrected" by extending one or more of the probes using a polymerase or a reverse transcriptase. Generally, extension of a probe hybridized to a DNA target is accomplished by a DNA polymerase or a Klenow fragment as is known in the art. In the case of an RNA target, extension is accomplished by a reverse transcriptase. Exemplary reverse transcriptases include those from avian myeloblastosis virus (AMV) and Moloney murine leukemia virus (M-MuLV) generally available to those skilled in the art. It is, of course, preferable to utilize extension reagents, such as TAq polymerase, which are thermally stable and can withstand the cycling of high temperatures required for LCR. If the extension reagent is not thermally stable, it typically must be re-added at each cycle of LCR.

Correction by extension in this manner requires the presence in the reaction mixture of deoxynucleotide triphosphates (dNTP's) complementary to the bases of the target in the gap region(s). More specifically, for a gap having the sequence $X_n$, the dNTP's that must be supplied are designated dX'TP wherein X' stands for the the complements of each base in the gap $X_n$. The dNTP's are commercially available from a number of sources, including Pharmacia (Piscataway, N.J.) and Bethesda Research Laboratories (Gaithersburg, Md.).

Extension must be terminated precisely at the point of ligation so that the extended probe abuts the adjacent probe and can be ligated to it. "Stopbases" are employed for this purpose, (See FIGS. 3 and 4). A "stopbase", designated Q', is defined in terms of its complement, Q and is accomplished by omitting from the reaction mixture, dNTP's that are complementary to Q; i.e. by omitting dQ'TP from the reaction mixture. Thus it is seen how the bases for the gap sequence(s) must be selected from a set, N, consisting of only three of the four bases, so that the complementary three of the four dNTP's are added to the reaction mixture. When the fourth dNTP, dQ'TP, is absent from the reaction mixture extension will terminate at the desired point of ligation. It follows that Q' is the first base in the adjacent probe, and the base on the target which codes for the stopbase is the first base adjacent the gap (on its 5' end in FIG. 3). It should be noted that the stopbase Q' itself (not the complement Q) must occur adjacent the 3' end of the $X_n$ gap. This is because a Q' stopbase must also be present to prevent undesired 3' end extension of probe B' (see FIG. 3).

Figure 1:
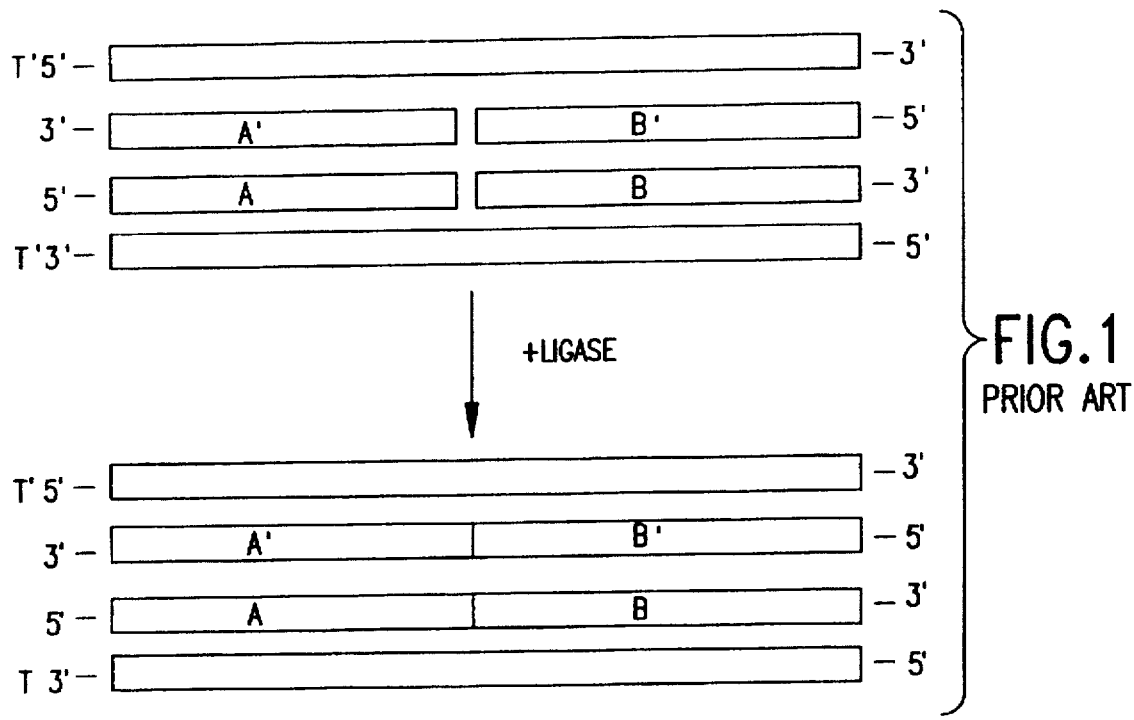
FIG. 1 is a graphic representation of the process of ligase chain reaction as it is known in the prior art.
Figure 3:
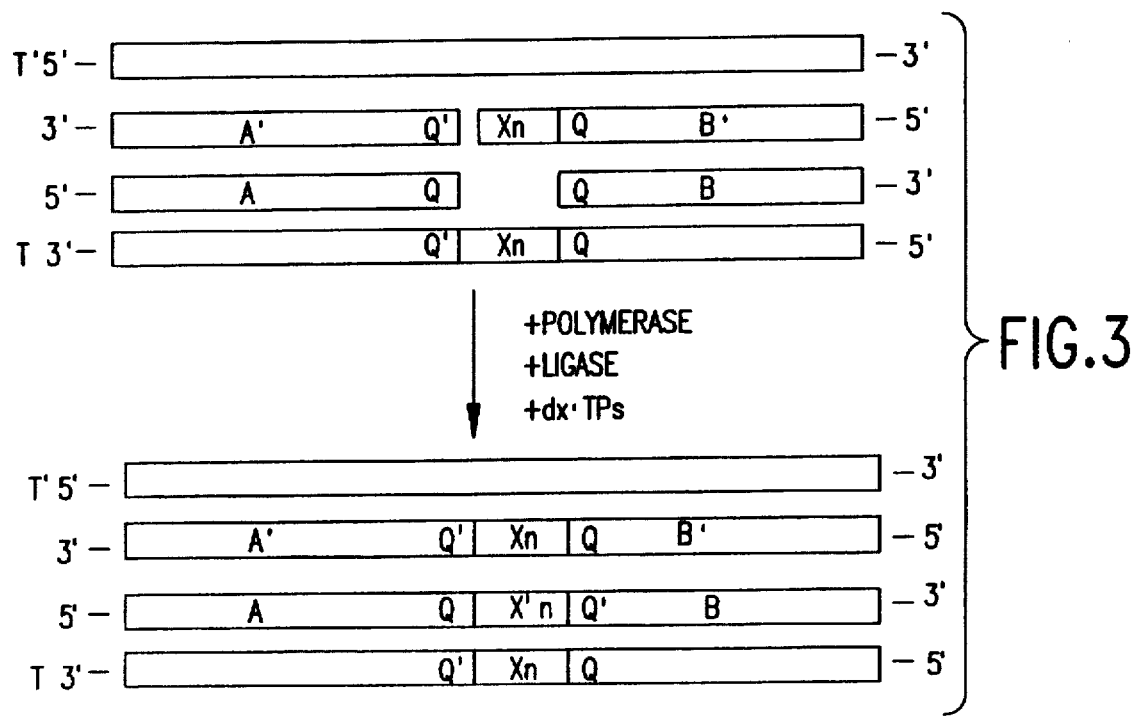
FIG. 3 is a graphic representation of the single gap variation of the second embodiment.
Figure 4:
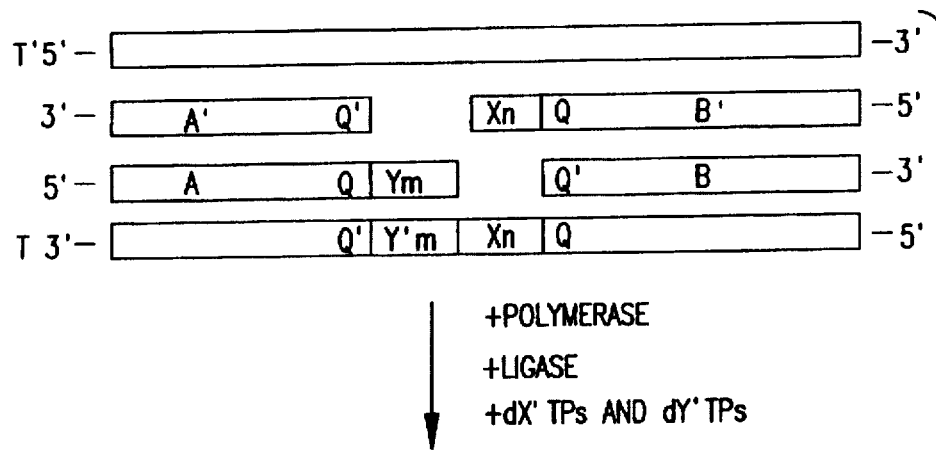
FIG. 4 is a graphic representation of a generalized, double gap variation of the second embodiment.
Figure 4:
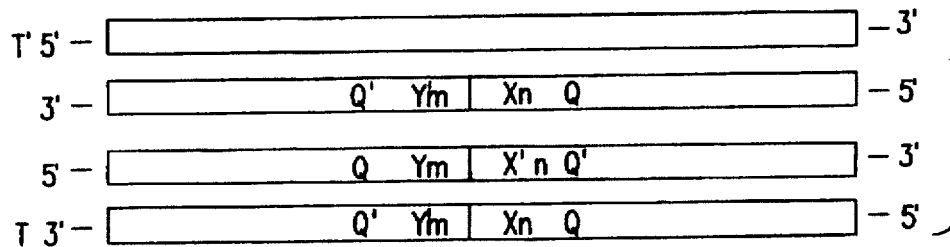

Since the concept is easiest to grasp in its simpler special case, the single gap method is described first. It should be understood, however, that the single gap variation is merely a special case of the double gap variation discussed later. FIG. 3 depicts an embodiment referred to as single gap since only one of the probes (namely B) has a gap at its 5' end. A first probe, A, hybridizes to a first segment of the target strand, T. A second probe, B, hybridizes to a second segment of the target strand, leaving a gap of one or more bases between the 5' end of the first segment and the 3' end of the second segment. This gap is designated $X_n$. A third probe, A', is hybridizable to the first probe A; and a fourth probe B' is hybridizable to the second probe B. As shown in FIG. 3, the target strand T can be double stranded, having a target complement, T'. In this case, probes A' and B' will participate in the initial hybridization by hybridizing to first and second segments of the target complement.

Extension by polymerase or transcriptase proceeds in a 5' to 3' direction. Consequently, the 3' ends of both A and B' would be extendable by polymerase in the absence of anything to prevent extension. If probe A' is hybridized in place on the target complement it sterically prevents extension of B'. If, however, A' is not hybridized to the target complement, extension still is terminated if the next base called for in the extension of B' (here Q') is absent from the reaction mixture. Conversely, Probe A is extended until either probe B or stopbase complement (Q) is encountered along the target strand. Since A' will not serve as a template for extension of A, probe A is extended only if hybridized to the target.

As alluded to above, it is important to terminate the extension of A at the end of the gap (i.e., at the point of ligation) so that the extended probe can be ligated to the 5' end of the adjacent probe, B. Therefore, the reaction mixture omits deoxynucleotide triphosphates complementary to the base immediately adjacent the 5' end of the gap $X_n$. Accordingly, $X_n$ can be any number of bases long, i.e., n can be any integer greater than or equal to 1. The only restriction on the bases X is that they be selected from a set N which consists of from 1 to any 3 of the four bases. At least one base must be reserved to code for the the stop base Q'. It should be understood, that when fewer than 3 bases are used in the $X_n$ sequence, any of the remaining bases can serve as the stop base. Thus, Q is selected from the set "not N" where "not N" consists of the four bases (the Universe) less any elements contained in set N.

It should now be apparent that the points of ligation in this embodiment are always the 5' ends of probes A' and B. It is not by mere coincidence that these are also the locations of the stopbases Q'.

Although more detailed examples are provided at the end of the specification, a general example will now be described. Suppose that in FIG. 3, the gap $X_n$ represents the sequence GA. The bases are thus selected from a set N (N={G,A}) which consists of two of the four bases. The dNTP's that must be added during probe extension are dCTP and dTTP. The stop base, Q', can be either G or A in this example and its complement, Q, must be either C or T. Accordingly, it is seen how the requirement that Q be selected from the set "not N" is fulfilled.

In the presence of a suitable polymerase, probe A is extended by the addition of C and T to its 3' end using the target strand as a template. However, when the polymerase encounters the C or T in the Q position on the template, it is unable further to extend probe A since neither G nor A are supplied to the reaction mixture as dNTP's. Extension terminates precisely at the point of ligation with the extended 3' end of probe A abutting the 5' end of probe B.

Next, a ligase is employed to join the 3' hydroxyl end of extended probe A to the 5' phosphate end of probe B to form a double stranded complex of fused or ligated primary probe and target strand. If the target is double stranded and has a complement T', the ligase will also join probes A' and B' in the initial cycle if they are hybridized to the target complement. If they are hybridized to excess probes A and B rather than target complement, ligation is inhibited since the ends are neither blunt nor sticky and there is no substrate for ligation.

Subsequently, the double stranded complexes are dissociated and new probes A, A', B and B' are permitted to hybridize to the target, the target complement, and both of the fused polynucleotides from the first cycle. Extension and ligation occur as before and the process can be repeated.

Exemplary combinations of bases for $X_n$, Q and Q' are given in Table I. It will be understood that the invention is not limited to these particulars combinations but these have been chosen as illustrative of many possible combinations. Table I also demonstrates the requirement that Q be selected from the bases represented by the set not N. This means that the stop base Q' must have as its complement, a base that fails to occur in the $X_n$ sequence.

TABLE I

ILLUSTRATIVE GAP SEQUENCES, REQUIRED
dNTPs, and POSSIBLE COMBINATIONS FOR Q and Q'
IN SINGLE GAP VARIATION

| $X_n$/N | X'TPs | not N* | STOPBASE Q' |
|---|---|---|---|
| A | T | T, C, G | A, C, G |
| GT | C, A | C, A | G, T |
| GC | G, C | A, T | A, T |
| AA | T | T, G, C | A, C, G |
| G CA | C, G, T | T | A |
| G CAG | C, G, T | T | A |
| AAATT | T, A | G, C | C, G |
| GCAGCA | C, G, T | T | A |
| GACT | all | VOID since no STOPBASE | |

*The set not N provides the possible complements (Q) for the stopbase Q'. The actual stopbase (Q') possibilities are given in the next column.

As previously mentioned, the single gap variation is a specialized case of the more generalized double gap variation wherein m=0. The double gap variation also employs four probes, A, A', B and B'. In this variation, as in the previous variation, the probe B' is shortened at its 5' end creating a gap of $X_n$ bases between the first and second segments of the target to which the primary probes A and B hybridize. The bases of gap $X_n$ are subject to the same limitations as in the single gap variation.

In addition, third probe A' is also shortened at its 5' end (see FIG. 4) with respect to both the target complement and the first probe A to create a second gap of $Y_m$ bases between the secondary (third and fourth) probes. Gap $Y_m$ can be any number of bases long and need not be the same length as $X_n$ i.e., m need not equal n.

Indeed, m may equal zero, in which case the double gap variation degenerates into the specialized case of the single gap.

In a preferred method of the invention, the fourth probe B' includes a 3' terminal sequence of $X_n$, identical to the $X_n$ sequence gap in the target. This arrangement is not essential to the invention, however, as the gap need only be formed between the probes. Thus, the 3' terminus of the fourth probe B' may stop short of the 3' end of sequence $X_n$, provided there is no 3' recessed end with respect to the second probe B. Since extension occurs in a 5' to 3' direction and dX'TPs must be supplied, probe B' would be extended through the gap, (both $X_n$ and $Y_m$) just as the first probe A is extended through the $X_n$ gap.

The method of the invention employing the double gap embodiment is very similar to that employed with the single gap embodiment. The steps of hybridization, extension and ligation remain essentially the same. Under conditions promoting extension, both the A and B' probes are extended from their 3' ends to fill the gaps $X_n$ and $Y_m$, respectively. Stopbases Q' terminate extension of both probes at the point of ligation and the probes are ligated to their now-adjacent associated probes.

There are, however, some restrictions on the base residues that can comprise the $Y_m$ sequence. Since at least one stopbase Q' must be maintained, the combined sets N and M which represent the possible bases for X and Y, respectively, must include no more than three of the four bases. Accordingly, Y can be from zero to any three of the four bases provided that at least one base remains in the set "not N and not M". If set N constitutes less than three of the four bases, then Y can be a base that is not within N so long as there is at least one base remaining, the complement of which can serve as the stopbase Q' for termination of probe extension. A single stopbase can serve to terminate extension in both the $X_n$ and $Y_m$ gaps.

A second limitation on sequence $Y_m$ occurs if m equals n. If the gaps are the same length, the sequence $Y_m$ should not be complementary to the sequence $X_n$ or the 3' ends of probes A and B' would constitute "sticky ends". "Sticky ends" would permit a target independent double stranded complex to form wherein probe A hybridizes to probe B' such that ligations and amplification would proceed. Rather, when m equals n it is preferred that $Y_m$ not be complementary to $X_n$. In other words, the ends of probes A and B' should at least be "slippery ends" which may be the same length, but are not complementary.

Nevertheless, even if target independent ligation and amplification occur, such as with sticky ends (or less likely with slippery ends), these fusion products are distinguishable from amplified target. In the case where m equals n, there is a small but finite chance that double stranded complexes of A:A' will ligate to double stranded complexes of B:B' independently of target. These complexes will be shorter than the desired target sequence by m (or n) bases and can be distinguished on the basis of length. In addition, if the ends are "slippery", the base mismatch can be detected by a number of reagents that are capable of detecting and/or destroying base mismatches. For example, base mismatches may be determined chemically by the hydroxylamine-osmium tetraoxide technique disclosed in Cotton, et al. *Proc. Natl. Acad. Sci.* 85:4397–4401 (1988); and may be determined enzymatically by reagents such as S1 nuclease and mung bean nuclease.

Some exemplary combinations of X's and Y's, their dNTP counterparts and the resultant possibilities for Q and Q' are given in Table II.

TABLE II

ILLUSTRATIVE GAP SEQUENCES, REQUIRED
dNTPs, and POSSIBLE COMBINATIONS FOR Q and Q'
IN DOUBLE GAP VARIATION

| $X_n$/N | $Y_m$/M | X'TPs | Y'TPs | not N and not M* | STOPBASE Q' |
|---|---|---|---|---|---|
| A | A | T | T | T, C, G | A, C, G |
| G | T | C | A | C, A | G, T |
| AT | AT | T, A | T, A | C, G | C, G |
| AC | GA | T, G | C, T | T | A |
| ATG | AAA | T, A, C | T | C | G |
| GGCC | AAACG | C, G | T, G, C | T | A |
| ATTGA | AGGT | T, A, C | T, C, A | C | G |
| CGC | GCG | complement. not permitted | | | |

*The set not N and not M provides the possible complements (Q) for the stopbase Q'. The actual stopbase (Q') possibilities are given in the next column.

The length of gaps $X_n$ and $Y_m$ may be zero ($Y_m$ only), one or any integer greater than one. For example, gaps of from 1 to 20 bases would be possible. Practically, however, gaps of much shorter length are preferred; for example from 1 to 3 or 5 bases. Most preferred at present are gaps of only a single base. It has been found that gaps of a single base greatly increase the ratio of true signal to background and leave the largest number of options for stopbases and dXTP's. Since probes are actually designed around existing targets, rather than "selecting" stopbases, a single base gap is more useful in most cases.

Further Features

In a variation of either "recessed" embodiment, the deoxynucleotide triphosphates used in filling the gaps may be modified to contain a marker moiety. Exemplary markers include direct labels such as radioisotopes, or hooks such as biotin, digoxin or other hapten capable of being recognized by either a solid phase or a label producing system. Isotopic labels include $^{32}$p, and deuterium among others.

Incorporation of the marker into the dNTP's is generally a matter of conventional organic chemistry. Linkers or spacers may be used but are not essential. It is only important that the modified dNTP be able to be incorporated into the gap opposite its complement on the target strand and be covalently bonded to the adjacent base.

Furthermore, either of the embodiments can be used to distinguish a first (or target) sequence from a second (or nontarget) sequence differing by a single base, Z, if the base difference is in either of two locations in the second strand. In both cases, a gap having only one base (constituency, not length) is used to distinguish single base differences.

First, a differing base, Z, occurring in the gap region of the nontarget can be distinguished by omitting dZ'TP from the reaction mixture. Accordingly, it may be said that Z must also belong to the set not N and not M. The differing strand will not be extended by polymerase since the appropriate nucleotide triphosphates are not supplied. It can be seen that the maximum ability to distinguish a different base Z occurs when a single gap is only one base long, leaving the largest possible set not N and not M.

Secondly, if the differing base Z is present in the position of Q, the strands can be distinguished because extension will not be properly terminated and the resulting extended product will be too long to ligate to its associated probe along the target strand. In this variation, maximum ability to distinguish occurs when there is only one possibility for the stopbase, all the others permitting a product that is too long.

The double gap embodiment is similarly useful for distinguishing a sequence having a single base difference at one or the other of the gaps. It can also be used to disthaving a sequence having a differing base in the stop base or Q' position.

2. Gap Filling by Additional Probes

According to this version of the recessed embodiment, the invention involves repeated steps of (a) hybridizing the modified probes to the target (and, if double stranded so that target complement is present, to the target complement); (b) providing fifth and sixth gap-filling probes to fill the gaps between primary and secondary probes; (c) ligating both ends of the gap-filling probes to the adjacent probes to form a fused or ligated product; and (d) dissociating the fused product from the target and repeating the hybridization, gap-filling and ligation steps to amplify the desired target sequence. In this embodiment probes D, D', E, and E' are used in place of the four probes A, A', B and ' (See FIG. 5). Fifth and sixth "gap-filling" probes F and ' are used in place of polymerase and dNTP's to fill in the recesses or gaps between the other probes.

Three pairs of probes are employed in this embodiment. First and second probes D and D', respectively will hybridize to one another, as will third and fourth probes E and E', respectively. (Note that the probe nomenclature in this embodiment differs from that used in the previous embodiment; i.e. here the second probe is the complement of the first, rather than its associated partner. Thus, the first and third probes become the primary probes.) When the primary probes D and E are hybridized to the target strand, there is a gap of at least one base, preferably several bases, between the 3' hydroxyl end of D and the 5' phosphate end of E. Similarly, when probes D' and E' are hybridized to the target complement T', there is a gap of one to several bases between them as well, although the gaps are not aligned. Thus, probes D and E, and probes D' and E' are modified to be non-adjacent as well as not blunt-ended (when duplexed with its complement). The gaps in this version are "corrected" by supplying fifth and sixth probes F and F', respectively which hybridize to the target and target complement (and to one another) between both primary and both secondary probes to fill in the gaps.

Figure 5:
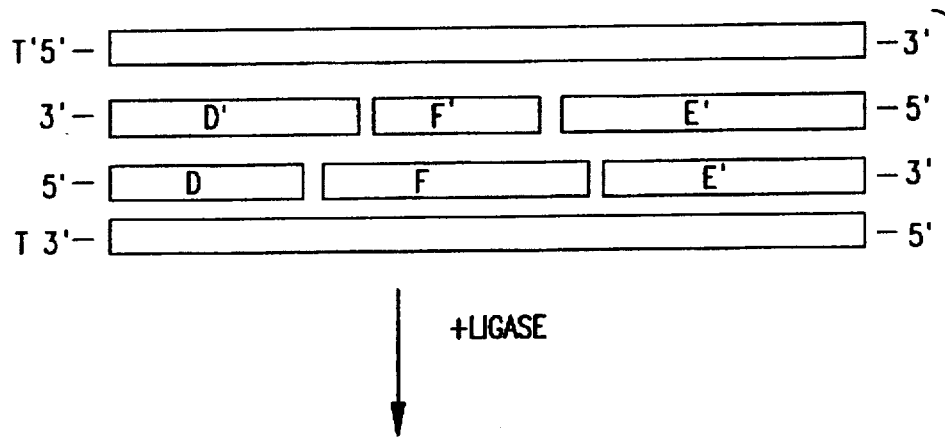
FIG. 5 is a graphic representation of a third variation of the second embodiment utilizing additional probes to fill the gaps.
Figure 5:
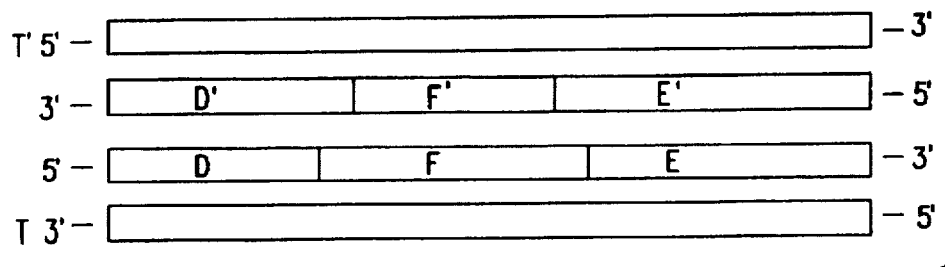

As seen in FIG. 5, it is preferred that one of the gap-filling probes be shorter on both ends than the other gap-filling probe. In other words, both secondary probes D' and E' extend past both of the respective primary probes or, alternatively, both primary probes extend past their respective secondary probes. Alternatively, as demonstrated in Example 13, one primary probe (D) may extend past its secondary complement (D'), while the other primary probe (E) stops short of its complement (E'). In this alternative configuration, however, it is important that the modified end not be "sticky" with respect to the "wrong" probes. For example, the 3' end of D which extends beyond D' should be complementary only with the the 3' end of F' which extends beyond F. It should not be complementary to the end of F which extends beyond F' or with the 3' end of E' which extends beyond E. If this precaution is not taken, the probe duplexes may reorganize in the absence of true target to produce high background signal.

The probes according to this embodiment can be manufactured in the same way as probes for the previous embodiment. Typically, probes will also be of comparable lengths as in the prior embodiment. Finally, reaction conditions which are useful with the above embodiment are also useful with this embodiment, with the exception that extension and polymerase are, unnecessary in this embodiment.

Once the gaps between the primary and secondary probes have been filled with the gap-filling probes, the gap-filling probes are ligated at both ends to the respective secondary or primary probes to form continuous polynucleotide strands. The primary probes and the first gap-filling probe F form a primary polynucleotide strand complementary to the target strand, while the secondary probes and the second gap-filling probe F' form a secondary polynucleotide strand complementary to the target complement strand. Of course, the primary polynucleotide and the secondary polynucleotide are also complementary to one another. Consequently, repeated cycles of hybridization and ligation produce an amplification of the target sequence just as in conventional LCR. In contrast, however, falsely positive signal arising from blunt-end ligation is significantly reduced by this embodiment since double stranded complexes D and D' cannot blunt-end ligate with double stranded complexes E and E'. This is due to the one or more bases omitted from both of the secondary probes or, alternatively, both of the primary probes.

It is understood, of course, that other products will be produced besides the desired polynucleotides. For example, it would be expected that shorter segments ("dimers") will form comprising D:F and D':F' or F:E and F':E'. It is further understood that these side or incomplete products will tend to utilize desired reagents. However, by adding excess reagents and by cleanly separating the desired polynucleotides from the incomplete products, the embodiment is useful, though not preferred at present.

Separation and detection of the ligated probes according to this version can be accomplished in any manner known in the art. A preferred method of detection employs markers attached to the primary or secondary probes. Preferably, a hook capable of being captured by a solid phase is attached to the 5' end of probe D, while a label or a hook capable of capturing label is attached to the 5' end of probe E'. The desired polynucleotide strand is then detectable by catching the first hook with the solid phase, separating the solid phase from the solution and detecting the label associated with the solid phase. Incomplete products formed during the reaction will be incapable of solid phase capture, or of label detection, or both. Thus, upon separation and detection, little or no signal is generated in the absence of target since blunt-end ligation cannot connect a capture hook with a label hook.

II. PCR

The principles of PCR have been fully described in the literature (see eg. U.S. Pat. Nos. 4,683,195 and 4,683,202); little additional detail is needed here. Fundamentally, a primer is hybridized to target and a polymerase extends or elongates the primer using nucleotide triphosphates as building blocks. The extension product (and its complement) serve as further templates for hybridization. Generally, for extension to occur, the 3' end of the primer must be perfectly complementary to the target. Many polymerases, including heat stable polymerases are known.

According to the present invention, the 3' ends of PCR primers are modified so that the primer is not extendable by a polymerase enzyme. Where these modifications can be removed in a template dependent manner, another level of stringency is added to the hybridization requirement for primer extension by the polymerase enzyme. This added level of stringency, particularly when both primary and secondary primers bear modified ends, effectively reduces spurious signal generation in PCR.

Many of the same general strategies useful for LCR regarding the choice of blocking groups and methods of correction may also be employed for PCR. Whereas in LCR the modification must block spurious ligation, in PCR the modification must block spurious elongation (extension). Thus, the modified or blocked 3' end, when hybridized to the target sequence, must not support elongation by a polymerase. To apply the descriptions of the LCR modified end embodiments given above, the terms "point of ligation" or "intented point of ligation" should be substituted with "point of elongation initiation"

A. OVERHANGING MODIFIED ENDS

Overhanging ends referred above to the relationship of complementary probes in the LCR situation. In the case of PCR, the term "overhanging ends" does not have a comparable meaning. For PCR, these modified ends are more aptly described as "template dependent blocking groups". Nevertheless, the "overhanging ends" modifications and corrections from LCR may generally be applied to PCR.

For chemical blocking modifications, all possible 'Z' moieties for the R group (with the possible exception of -deoxyribose) which are useful in LCR can also be used to block polymerization in PCR. In addition, identical correction mechanisms employing endonuclease IV may be employed for PCR.

"Overhang" modifications for LCR (consisting of additional nucleic acids beyond the point of intended ligation) were presented above. They are:

1. essentially ribonucleotide overhangs,
2. Abasic site overhangs, and
3. an overhang with a mismatched base.

While these modifications would seem to be disfavored for PCR, each of the overhang classes of modified ends may also be employed in PCR in an analogous manner, provided the overhang to be corrected (cleaved) can itself be rendered inactive as a substrate for an extension enzyme (eg. polymerase). If the overhang is not inactivated, it may, when cleaved, act as a primer for subsequent unwanted extension. A typical method of inactivating the overhang is to render the 3' terminus unsuitable for recognition by the extension enzyme. The modifications mentioned above in connection with the primer generally will inactivate the 3' end of the overhang as well. However, unlike modifications to the primer, modifications to the 3' end of the overhang should not be correctable by the same mechanism which is used to correct the primer modification. Otherwise both might be corrected simultaneously. Suitable modifications which are not easily corrected include a terminal dideoxynucleotide, cordecepin, or any other chemical modification either known or to be discovered which will realtively permanently prevent primer extension from the 3' terminus.

As in the case of LCR, these modifications are corrected in a template dependent fashion. The correction methods and reagents are the same as in LCR.

B. ENDS MODIFIED BY RECESSES

It is not presently known to us if or how recessed end modifications may be useful to reduce spurious signal development in PCR.

Following selection of a modification strategy, appropriate primers with modified ends are prepared. Conditions for hybridization of primers to target DNA are the same as for standard PCR and are found in the literature. Subsequent cycles of elongation, denaturation, and rehybridization are also the same as for standard PCR, differing only in the inclusion of an enzyme or other agent for correcting the modified end in a target dependent manner.

EXAMPLES

The invention will now be described further by way of examples. The examples are illustrative of the invention and

19 are not intended to limit it in any way. Unless otherwise indicated, probe and target sequences in the examples are written with the 5' end toward the left.

Example 1

The following duplex target DNA sequence is presented as only a single strand for simplicity sake. The "-" in the sequence represents the intended point of ligation of the LCR probes.

3'- . . . TTMGCTCGAGCCATGGG-
CCCCTAGGAGATCTCAGCTGGACGT . . . -5'

The following probe set was designed to detect the above target sequence by LCR, with reduced background levels.

A 5'-AATTCGAGCTCGGTACCC<u>p</u>

A'3'-GCTCGAGCCATGGG

B 5'-GGGGATCCTCTAGAGTCGACCTGCA

B'3'-<u>p</u>CCCCTAGGAGATCTCAGCTG

The probe set features two probes (A & B') containing terminal 3' phosphate blocking groups (underlined).

LCR reactions are performed (substantially as described in EP-A-320 308) using various amounts of target (pUC19). After the hybridization step of each cycle, endonuclease IV purified from *E. coli* is added to the reaction. this can be done under standard LCR conditions, since *E coli* endonuclease IV is somewhat thermostable. As a control, the LCR is run using the same number of target molecules without the addition of endonuclease IV. In these controls a probe set similar to the one shown above is used, only the 3' terminal nucleotides (containing the 3' phosphates) are not included on probes A and B'.

In both the experimental and control reactions, the rate of appearance of ligated product is correlated with the initial number of target molecules added. What distinguishes the two protocols is that in the second case, a "blank" tube containing no target molecules gives rise to signal at about the same rate as a tube containing 1000 target molecules, whereas in the case where modified probes and endonuclease IV are used, a "blank" tube containing no target molecules gives rise to signal significantly more slowly than does a tube containing 1000 target molecules.

This suppression of background provides an advantage in increasing the usable range of sensitivity of the assay.

Those skilled in the art will immediately appreciate the desirability of employing a highly thermostable endonuclease IV, for the same reasons that highly thermostable ligases and polymerases are useful and desirable in LCR and PCR, respectively. Those skilled in the art will also appreciate that other enzymes, either known or not yet known, which can remove modifications at the 5' or 3' ends of a DNA strand in a template dependent manner leaving the previously blocked 5' phosphate or 3' hydroxyl intact, can be employed in a manner completely analogous to endonuclease IV as described above.

Example 2

The following probe set can be used to detect the target DNA of example 1 with reduced background.

A 5'-AATTCGAGCTCGGTACCC

A'3'-GCTCGAGCCATGGGrCrCCC

B 5'-TA<u>CrCrC</u>GGGGATCCTCTAGAGTCGACCTGCA

B'3'-CCCCTAGGAGATCTCAGCTG

Probes A' and B contain chimeric ribo/deoxyribonucleotide extensions (bold and underlined). The ribonucleotide bases are preceeded with a lower case "r". LCR reactions are performed as in example 1 with the substitution for Ribonuclease H for endonuclease IV. For controls the same control probe set may be used as in example 1.

20

Results and interpretation are the same as example 1.

Example 3

The following probe set can also be used to detect the target DNA of example 1 with reduced background.

A 5'-AATTCGAGCTCGGTACCCJG

A'3'-GCTCGAGCCATGGG

B 5'-GGGGATCCTCTAGAGTCGACCTGCA

B'3'-GJCCCCTAGGAGATCTCAGCTG

Probes A and B' contain extensions (underlined,boldface type) featuring an abasic site ("J") followed by a standard nucleotide. LCR reactions are performed as in example 1. Results and interpretation are the same as in example 1.

Example 4

The following probe set can also be used to detect the target DNA of example 1 with reduced background.

A 5'-AATTCGAGCTCGGTACCC

A'3'-GCTCGAGCCATGGGAC

B 5'-CAGGGGATCCTCTAGAGTCGACCTGCA

B'3'-CCCCTAGGAGATCTCAGCTG

Probes A and B' contain dinucleotide extensions (underlined, boldface type) which when hybridized to the template DNA feature a first nucleotide A/G mismatch and a hybridizable second nucleotide. LCR reactions are performed as in example 1 with the substitution of an A/G mismatch repair enzyme (complex) for endonuclease IV. Results and interpretation are the same as in example 1.

Example 5

Haplotype 3 Phenylketouria (PKU) accounts for about 38% of all PKU alleles in one Danish study group. It is caused by a single base mutation (G>A) at the 5' splice donor site of intron 12 in the gene sequence encoding phenylalanine hydroxylase (PAH). The mismatch repair methodology for background reduction as outlined in example 4 can also serve as a sensitive assay for the determination of the presence or absence of this genetic defect in samples of blood or other fluids from individuals suspected of carrying this trait.

Probes having the end portions specified below are prepared complementary to the following target DNA from intron 12 of the PAH gene:

| | | |
|---|---|---|
| 3'- . . . TTTAATGAATGACAATTACCT . . . -5' | | normal PAH DNA |
| 3'- . . . TTTAATGAAT<u>A</u>ACAATTACCT . . . -5' | | PKU DNA |
| A | 5-. . . AAATTACTTA | |
| A' | 3-. . . TTTAATGAATAAC | |
| B | 5-<u>CT</u>GTTMTGGA . . . | |
| B' | 3-<u>G</u>ACAATTACCT . . . | |

The probes are designed according to standard LCR considerations (i.e. 15–30 mers), with the addition of single nucleotide extensions on B and B'. These extensions (relative to target DNA) consist of a first mismatched nucleotide followed by two hybridizable nucleotides.

Human DNA is purified from the blood of a subject to be tested for presence of PKU. It may be desirable to shear the DNA to an average size of <10 kb. The sample is subjected to LCR, with the above probes and addition of AG mismatch repair system enzyme(s) after the hybridization step of each cycle (see example 4). If the sample contains no wild type allele, the appearance of LCR reaction product, if any, will be significantly delayed compared to a standard LCR reaction using unmodified probes. If on the other hand, the wild

21 type allele is present, rapid appearance of fused probes from the LCR reaction will occur.

Example 6

Single gap LCR extension was performed for 80 cycles, each cycle consisting of a 30 second incubation at 85° C. and a 20 second incubation at 50° C. using a Coy thermocycler (Key Scientific). Cycle number was chosen to maximize the blunt end ligation background. Reactions were set up with either 0 or $10^6$ target DNA molecules. The target DNA was ScrF1 digested HPV 16 genomic DNA cloned into a pGEM vector. Each reaction also contained 10 nanograms of human placental background DNA. Two reactions were performed using standard blunt end oligonucleotides and two were performed using a single gapped set of oligonucleotides. Standard blunt end LCR reactions were run in a buffer containing 50 mM EPPS pH7.8, 100 mM KC1, 10 mM $MgCl_2$, 1 mM DTT, 10 mM $NH_4Cl$, 100 uM AND, 10 ug/ml BSA, $5 \times 10^{11}$ molecules each oligonucleotides A and ' (Table 6a), $7.5 \times 10^{11}$ molecules each oligonucleotides B and A'(Table 6a), and 1× *Thermus thermophilus* DNA ligase. Gapped LCR reactions were performed in the identical buffer except that oligonucleotide A' replaced A', and 25 mM 2'-deoxyadenosine 5'-triphosphate and 1.25 units Taq DNA polymerase were added. The oligonucleotides are specific for map positions 5695–5744 on the HPV 16 genome. In all cases, reaction volume was 50 ul and the reaction was overlaid with 25 ul of mineral oil prior to cycling.

TABLE 6a

| Oligonucleotide | |
|---|---|
| A | FL- AAGTTGTAAGCACGGATGAATATGT |
| A' | CATATTCATCCGTGCTTACAACT |
| A" | ACATATTCATCCGTGCTTACAACT |
| B | TGCACGCACAAACATATATTATCA-BIO |
| B' | BIO- ATGATAATATATGTTTGTGCGTGCA |
| C | FL- ATTTATACATTAAAGGCTCTGGGTC |
| C' | ACCCAGAGCCTTTAATGTATAAA-FL |
| D | ACTGCAAATTTAGCCAGTTCAA-BIO |
| D' | BIO- TTTGAACTGGCTAAATTTGCAGTA |

Following amplification, reactions were diluted 1:1 with sterile $dH_2O$, and the double labelled LCR amplification products were detected via a sandwich immunoassay performed on a prototype of the Abbott IMx system with results as follows.

| Number of Molecules | Rate (c/s/s) |
|---|---|
| 0 Standard LCR | 911.3 |
| $10^6$ Standard LCR | 925.9 |
| 0 Modified LCR | 62.0 |
| $10^6$ Modified LCR | 985.4 |

Example 7

Double gap LCR extension was performed for 35 cycles using a COY thermocycler (Key Scientific). Incubation times were identical to those above. Reactions were set up with either 0, $10^3$, or $10^6$ target molecules. The target DNA was ScrF1 digested HPV 16 genomic DNA cloned into a pGEM vector. Each reaction also contained 10 nanograms of human placental background DNA. Reaction conditions were identical to single gap extension experiments described in Example 6 above except each reaction contained $5 \times 10^{11}$

22 molecules each oligonucleotides C and D' (See Table 6a, above), $7.5 \times 10^{11}$ molecules each oligonucleotides D and C', and 25 mM each 2'-deoxythymidine 5'-triphosphate and 2'-deoxyguanosine 5'-triphosphate. The oligonucleotides are specific for map positions 6457–6505 on the HPV 16 genome.

Following amplification, reaction products were diluted 1:1 with sterile $dH_2O$, and the double labeled LCR amplification products detected via a sandwich immunoassay performed on a prototype of the Abbott IMx system with results as follows.

| Number of Molecules | Rate (c/s/s) |
|---|---|
| 0 | 15.44 |
| $10^3$ | 42.47 |
| $10^6$ | 1375.19 |

Example 8

Gaps of greater than 1 base can be used for LCR extension. For example, the oligonucleotide TATTCATCCGT-GCTTACAACT (herein oligo E) could replace the HPV 16 specific oligonucleotide A' of Table 6a in the LCR set (A, A', B, and B') used for amplification of HPV 16 sequences described in Example 6. When hybridized to the appropriate single strand HPV 16 target sequence, oligonucleotides B and E would be separated by a 3 nucleotide gap. Amplification reaction conditions would be identical to those described except that 2'-deoxcytidine 5'-triphosphate would need to be included in addition to dATP to completely fill the 3 nucleotide gap. Gaps of different sizes can also be examined in a similar manner in both the single and double gap format.

Example 9

Approximately 70% of mutant alleles of the cystic fibrosis gene exhibit a single trinucleotide deletion in exon 10 (Riordan, J. R. et al *Science* 245:1066 1989; Kerem, B. et al *Science* 245:1073 1989.) The oligonucleotides listed in Table 9a below could be used for single gap LCR amplification of both the normal (oligonucleotides A, A', B, and B') and mutant (oligonucleotides C, C', B, and B') alleles of the CF gene.

TABLE 9a

| A | Fl-CACCATTAAAGAAAATATCATCTT |
|---|---|
| A' | AAGATGATATTTTCTTTAATGGTGC-Fl |
| B | GGTGTTTCCTATGATGAATATAGA-BIO |
| B' | BIO-CTATATTCATCATAGGAAACACCA |
| C | FL-TGGCACCATTAAAGAAAATATCAT |
| C' | ATGATATTTTCTTTAATGGTGCCAG-FL |

The LCR oligonucleotides A, A', B, and B' were used for amplification of wild type sequences of the cystic fibrosis gene from human placental DNA. Reactions were set up with either no targetbackground DNA or with 1.5 ug of human placental DNA. Duplicate reactions were run in an identical buffer as described in Example 6 containing $5 \times 10^{11}$ molecules each of oligonucleotides A and B', $7.5 \times 10^{11}$ molecules each oligonucleotides A' and B, 25 mM 2'-deoxythymidine 5'-triphosphate, and 1.25 units of Taq DNA polymerase for 30 cycles. Double labeled amplification products were detected as described.

| Target | Rate (c/s/s) |
|---|---|
| No Target | 9.3 |
| Placental DNA | 738.5 |

Example 10

Oligonucleotides A, A', B, and B' (Table 6a) could be varied in length from 17–35 nucleotides. Initial experiments will focus on the 19-mer and 30-mer oligonucleotide sets listed in Table 10a. The actual upper and lower limits of oligonucleotide size can be determined experimentally. The procedure of Example 6 is repeated, using the probes of Table 10a for single gap LCR extension. Similar studies can be performed with the double gap oligonucleotide set.

TABLE 10a 19-mer set

A: Fl-TAAGCACGGATGAATATGT

A': CATATTCATCCGTGCTTAC

B: TGCACGCACAAACATATAT-BIO

B': BIO-ATATATGTTTGTGCGTGCA 30-mer set:

A: Fl-TATCTAAGTTGTAAGCACGGAT(AATATGT

A': CATATTCATCCGTGCTTACAACTTAGATAC

B: TGCACGCACAAACATATATTATCAGCAGG-BIO

B'': Bio-CCTGCATGATAATATATGTTTCTGCGTGCA

Example 11

Single and double gap LCR extension allows the use of increased cycle numbers since the blunt end ligation background is greatly reduced. The reduction in background as well as the use of additional cycles of LCR is expected to greatly enhance the sensitivity of the LCR technique. Oligonucleotides A, A', A'', B, and B'(Table 6a) could be used for blunt end and single gap LCR for various cycle numbers in order to determine the extent of sensitivity enhancement. Reaction conditions would be identical to those described in Example 6 except that replicate positive and negative reactions would be examined after 20, 25, 30, 35, 40, 45, and 50 cycles. Similar experiments could be performed using even more cycles if desired, and/or using the double gap LCR extension set described in Example 7.

Example 12

The ability of single gap LCR extension to distinguish single base mismatches was examined using synthetic HPV 16 oligonucleotide target sequences. The oligonucleotides (A, A', B, and B') used for amplification are listed in Table 6a of Example 6. The synthetic target sequences used are listed in Table 12a below.

Target sequence $_A$ (Table 12a) represents wild type HPV sequences specific for map positions 5695–5744 on the HPV 16 genome. Target sequence $_B$ is identical to sequence $_A$, except that the thymidine at base position 25 which acts as a template for gap filling with dATP is changed to an adenine. Therefore, oligonucleotide B' (Table 6a, Example 6) cannot be extended under the conditions described in example 6 when hybridized to this target sequence. Target sequence $_C$ is identical to sequence $_A$ except for a single G to T change at the stopbase (target base position 24). When hybridized to this target sequence, oligonucleotide B' will be extended by 3 bases. Therefore, extension will occur beyond the gap region.

Synthetic Targets

A AAGTTGTAAGCACGGATGAATATGTTG-CACGCACAAACATATATTATCA

B AAGTTGTAAGCACGGATGAATATGATG-CACGCACAAACATATATTATCA

C AAGTTGTAAGCACGGATGAATATTTTG-CACGCACAAACATATATTATCA

Reactions were set up in triplicate with human placental background DNA (no target control) and placental DNA containing $10^6$ molecules of a given synthetic target. Reaction conditions were identical to those described in Example 6. Single gap LCR extension was performed for 50 cycles. Following amplification, reaction products were diluted 1:1 with sterile $dH_2O$, and the double labeled LCR reaction products were detected via a sandwich immunoassay performed on a prototype of the Abbott IMx system with the following results.

| Target | Rate (c/s/s) |
|---|---|
| No target | 15.2 |
| Target A | 167.7 |
| Target B | 8.2 |
| Target C | 12.5 |

Example 13

In another embodiment of the gap filling technique, additional probes can be used to fill the gap replacing the use of dNTPs and DNA polymerase. Probes to be used are listed in Table 13a below and are specific for map positions 5670–5743 on the HPV 16 genome. Oligonucleotide designation is according to the text.

TABLE 13a

| D | Fl-TACCTGCCTCCTGTACCTGTATCTA |
|---|---|
| D' | AGATACAGGTACAGGAGGCAGGTA-Fl |
| F | AAGTTGTAAGCACGGATGAATATG |
| F' | ATATTCATCCGTGCTTACAACTTT |
| E | TTGCACGCACAAACATATATTATCA-Bio |
| E' | Bio-TGATAATATATGTTTGTGCGTGCAAC |

LCR would be performed for various cycle numbers using incubation times and reaction conditions identical to those described in Example 6 except that dATP and DNA polymerase would no longer be required. It should be noted that oligonucleotides of different lengths (e.g. 17–35 nucleotides) could also be used. All oligonucleotides would be present in the reaction at $5.0-75\times10^{11}$ each. Following amplification, reaction products would be diluted and detected as described in previous examples.

EXAMPLE 14

The following synthetic oligonucleotides are prepared and used as primers for a PCR reaction, with pUC18 as the intended target DNA.

| Primer | Complementary to pUC18(nt)* |
|---|---|
| A 5'-AATTCGAGCTCGGTACCC | 498–481 |
| B 5'-CTGAGAATAGTGTATGC | 2239-2255 |

In addition, modified primers $A_{mod}$ and $B_{mod}$, which contain abasic sites are prepared. These primers are used to replace primers A and B respectively. The sequences of the modified primers and their complementarity to pUC18 DNA is as follows:

| Primer | Complementary to pUC18(nt)* |
|---|---|
| $A_{mod}$ 5'-AATTCGAGCTCGGTACCCJGGGATCCX | 498-473 |
| $B_{mod}$ 5'-CTGAGAATAGTGTATGCJGCGX | 2239-2259 |

*The nucleotide (nt) numbering system refers to that published by DNA Star Inc, (Madison, WI).

The experimental oligonucleotides consist of the original sequences (A or B above) modified to include a single abasic residue (J) and additional nucleotides complementary to the pUC18 target.

Methods for preparing oligonucleotides containing abasic residues are given by Takeshita, et al., supra. The 3' terminus of the modification (the "overhang") is inactivated by including a dideoxy adenosine (X) residue, such as by terminal transferase as described by Berger, et al., *Guide to Molecular Cloning Techniques*, p. 104 (1987).

PCR is performed according to the method of Mullis, et al (see eg U.S. Pat. Nos. 4,683,195 and 4,683,202), with the presence of $^{32}$P-dCTP in the nucleotide mixture. Where indicated below, the enzyme Endonuclease IV (Endo IV) is added to the reaction mixture following the hybridization step of each cycle.

Following PCR, the amplification products are precipitated with trichloroacetic acid (TCA), washed, and the signal is measured. The following table gives the anticipated relative signal intensity for the various reaction schemes.

| Primer mix | with target DNA | without target DNA |
|---|---|---|
| A + B | +++ | ++ |
| $A_{mod}$ + $B_{mod}$ + Endo IV | +++ | – |
| $A_{mod}$ + $B_{mod}$ – Endo IV | – | – |
| A + B, no polymerase | – | – |

What is claimed is:

1. In a method of amplifying a target nucleic acid sequence enzymatically, wherein an enzyme utilizes a nucleic acid initiator; the target sequence to which it hybridizes as a template; and additional nucleosides to enzymatically assemble amplification products complementary to the target, the amplification products themselves serving as further templates; the improvement comprising:
   (a) providing requisite initiators capable of hybridizing with the target, wherein at least one of the initiators is modified such that, when the initiator is hybridized, the enzyme is substantially incapable of recognizing the initiator as its substrate, so that amplification product is not assembled;
   (b) hybridizing the initiator to the target, if present, to form an initiator-template complex;
   (c) correcting the modification in a target dependent manner to render the initiator-template complex recognizable by the enzyme;
   (d) enzymatically assembling an amplification product; and
   (e) dissociating the amplification product from the target and repeating the hybridization, correction and assembling steps to amplify the desired target sequence.

2. The method of claim 1 wherein said modification of at least one initiator (step a) comprises a blocking moiety attached to said initiator such that it blocks a chemical group required in the enzymatic assembly of step d.

3. The method of claim 2 wherein the blocking moiety is of the form:

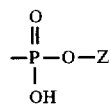

wherein Z is selected from the group consisting of —H;— $(CH_2)_n$ CHO, where n is from 1 to about 3;,-deoxyribose; and -dideoxyribose.

4. The method of claim 3 wherein said correction of the modification comprises the use of endonuclease IV.

5. The method of claim 2 wherein said blocking moiety is a nucleic acid overhang, provided that if the enzymatic assembly of step d occurs by extension, the overhang includes a non-extendable 3' terminus.

6. The method of claim 5 wherein said probes comprise deoxyribonucleotides and said overhang comprises ribonucleotides.

7. The method of claim 5 wherein said overhang comprises at least one abasic residue.

8. The method of claim 5 wherein said overhang comprises a nucleic acid base residue selected so that, upon hybridization of the initiator with a target strand, a base pair mismatch results.

9. The method of claim 6 wherein said correction of the modification comprises the use of an RNAse H enzyme.

10. The method of claim 7 wherein said correction of the modification comprises the use of an endonuclease that cleaves a nucleic acid strand at an abasic site substantially only when the strand is hybridized to a complementary strand.

11. The method of claim 8 wherein said correction of the modification comprises the use of a mismatch repair enzyme.

12. The method of claim 1 wherein the enzyme is a polymerase and the amplification product comprises an extension product made from primer and nucleoside triphosphates.

13. The method of claim 1 wherein the enzyme is a ligase and the amplification product comprises fused oligonucleotides.

14. The method of claim 13 wherein the modified initiator (s) of step (a) include a first probe hybridizable to a first segment of the target, a second probe hybridizable to a second segment of the target, a third probe hybridizable to the first probe and a fourth probe hybridizable to the second probe, wherein, as the modification;
   (i) the 5' end of the first segment of the target is spaced from the 3' end of the second segment by $X_n$ bases, each X being independently selected from a set N consisting of from one to any three of the four bases, and n being any integer greater than or equal to 1;
   (ii) the third probe hybridizes to the first probe, such that the base on the first probe complementary to the 5' end of the third probe is spaced from the 3' end of the first probe by $Y_m$ bases, each Y being independently selected from a set M consisting of from zero to any three of the four bases, and m being zero or any integer greater than or equal to 1, provided that at least one base remains unused in the $X_n$ and $Y_m$ sequences to comprise the set not N and not M, and that the sequence of $X_n$ bases is not complementary to the sequence of $Y_m$ bases; and
   (iii) the base adjacent the 5' end of $X_n$ and the base adjacent the 5' end of $Y_m$ are selected from a set Q, which consists of not N and not M;

and wherein said step (c) comprises extending the first probe to fill the $X_n$ gap, and optionally the fourth probe to fill the $Y_m$ gap, using an excess of deoxy X' triphosphates and deoxy Y' triphosphates, wherein X' and Y' represent the complements of X and Y, respectively.

15. The method of claim 14 wherein n equals from 1 to about 3.

16. The method of claim 15 wherein m equals zero.

17. The method of claim 14 wherein the deoxy X' triphosphates added during step c comprise bases modified to contain a marker selected from the group consisting of labels, hooks and haptens.

18. The method of claim 13 wherein the initiators of step (a) include three pairs of complementary probes which hybridize to the target and, optionally, the target complement, including (i) a first probe, D, hybridizable to a first segment of the target, and a second probe, D', hybridizable to the first probe D such that the 3' end of the second probe D' overhangs the 5' end of probe D by at least one base;

(ii) a third probe, E, hybridizable a second segment of the target and a fourth probe, E', hybridizable to the third probe, E, such that the 5' end of probe E' overhangs the 3' end of probe E by at least one base; and (iii) a fifth probe, F, hybridizable to a third segment of the target and a sixth probe, F', hybridizable to the fifth probe, F;

wherein the first, third and second segments of the target are consecutive such that, when hybridized to the target, the fifth probe lies with its 3' end adjacent the 5' end of the first probe, and with its 5' end adjacent the 3' end of the third probe, and wherein, as the modification, the 3' end of the fifth probe, F, overhangs the sixth probe, F', by a base sequence complementary to and the same length as the sequence by which the second probe, D', overhangs the first probe, D; and the 5' end of fifth probe, F, overhangs the sixth probe, F', by a base sequence complementary to and the same length as the sequence by which the fourth probe, E', overhangs the third probe, E;

and wherein said step (c) comprises ligating the fifth probe, F, to both the first probe, D, and the third probe, F in a target dependent manner to form a single fused polynucleotide and, optionally, ligating the sixth probe, F', to both the second probe, D', and the fourth probe, F', in a target-complement dependent manner to form a second fused polynucleotide complementary to the target complement.

19. The method of claim 18 wherein the overhangs of the second and fourth probes, D' and E', respectively, independently comprise form 1 to about 3 bases.

20. The method according to claim 18, and comprising the further step of detecting the presence of amplified target sequences by means of markers attached to the 5' ends of the second and third probes.

21. The method according to claim 20, wherein the marker comprises biotin, dansyl or fluorescein.

22. A method of determining the allelic identity of a particular base in a nucleic acid sequence comprising:

(a) providing two pairs of probes, each pair comprising a primary probe hybridizable to the target and a secondary probe hybridizable to the primary probe, the primary probe of each pair hybridizing to adjacent or nearly adjacent segments of the target, wherein at least one of the primary or secondary probes is modified at one end to contain a nucleotide extension which blocks participation in a ligase reaction, said nucleotide extension containing a base chosen so that upon hybridization with the target nucleic acid strand, at the site of the allele to be tested, a mismatched base pair may result;

(b) hybridizing the probes to the target and, optionally, to the target complement;

(c) correcting the modification when the probe is hybridized to the particular allele, by enzymatic cleavage of the extension from the remainder of the probe at the locus of said chosen base to expose an end capable of participating in the ligase reaction;

(d) ligating the corrected probe to the adjacent probe partner to form a fused or ligated product; and (e) detecting the presence of ligated probe as a determination of the presence of the allele.

23. A method for distinguishing a first, target nucleic acid sequence from a second, nontarget sequence which differs from the target by the identity of at least one base, said method comprising:

a. providing an excess of each of four probes, a first probe complementary to a first segment of the target, a second probe complementary to a second segment of the target, a third probe complementary to the first probe and a fourth probe complementary to the second probe, (i) wherein the 5' end of the first segment of the target is spaced from the 3' end of the second segment by $X_n$ bases, each X being independently selected from a set N consisting of from one to any three of the four bases, and n being any integer greater than or equal to 1;

(ii) wherein the third probe hybridizes to the first probe, such that the base on the first probe complementary to the 5' end of the third probe is spaced from the 3' end of the first probe by $Y_m$ bases, each Y being independently selected from a set M consisting of from zero to any three of the four bases, m being zero or any integer greater than or equal to 1, provided that at least one base remains unused in the $X_n$ and $Y_m$ sequences, and that the sequence of $X_n$ bases is not complementary to the sequence of $Y_m$ bases;

(iii) wherein the base adjacent the 5' end of $X_n$ and the base adjacent the 5' end of $Y_m$ are selected from the set Q, which consists of not N and not M; and (iv) wherein the nontarget sequence differs by the identity of at least one base, Z, in the $X_n$ region or the $Y_m$ region;

b. combining said four probes under hybridizing conditions with single stranded target or double stranded target or double stranded target separated from its complementary strand;

c. while hybridized to target, extending the first probe to fill the $X_n$ gap, and optionally the fourth probe to fill the $Y_m$ gap, using an excess of deoxy X' triphosphates and deoxy Y' triphosphates, wherein X' and Y' represent the complements of X and Y, respectively, on the target strand but omitting deoxy Z' triphosphates complementary to the single different base in the nontarget gap;

d. while hybridized to target, ligating the extended first probe to the second probe, and optionally ligating the extended fourth probe to the third probe, to form at least one double stranded complex of ligated probe hybridized to the target sequence; and e. separating and detecting the properly extended and ligated probes from the improperly extended, unligated probes.

24. A method for distinguishing a first, target nucleic acid sequence from a second, nontarget sequence which differs from the target by the identity of at least one base, said method comprising:

a. providing an excess of each of four probes, a first probe complementary to a first segment of the target, a second probe complementary to a second segment of the target, a third probe complementary to the first probe and a fourth probe complementary to the second probe, (i) wherein the 5' end of the first segment of the target is spaced from the 3' end of the second segment by $X_n$ bases, each X being independently selected from a set N consisting of from one to any three of the four bases, and n being any integer greater than or equal to 1;

(ii) wherein the third probe hybridizes to the first probe, such that the base on the first probe complementary to the 5' end of the third probe is spaced from the 3' end of the first probe by $Y_m$ bases, each Y being independently selected from a set M consisting of from zero to any three of the four bases, m being zero or any integer greater than or equal to 1, provided that at least one base remains unused in the $X_n$ and $Y_m$ sequences, and that the sequence of $X_n$ bases is not complementary to the sequence of $Y_m$ bases;

(iii) wherein the base adjacent the 5' end of $X_n$ and the base adjacent the 5' end of $Y_m$ are selected from the set Q, which consists of not N and not M; and (iv) wherein the nontarget sequence differs by the identity of at least one base, Z, in the Q region, such that Z is a base contained in the set N, the set M or both;

b. combining said four probes under hybridizing conditions with single stranded target or double stranded target or double stranded target separated from its complementary strand;

c. while hybridized to target, extending the first probe to fill the $X_n$ gap, and optionally the fourth probe to fill the $Y_m$ gap, using an excess of deoxy X' triphosphates and deoxy Y' triphosphates, wherein X' and Y' represent the complements of X and Y, respectively, whereby Z fails to terminate extension of the first and optional fourth probes;

d. while hybridized to target, ligating the properly extended first probe to the second probe, and optionally ligating the properly extended fourth probe to the third probe, to form at least one double stranded complex of ligated probe hybridized to the target sequence; and e. separating and detecting the properly extended and ligated probes from the improperly extended, unligated probes.

25. A diagnostic kit comprising in combination:

(a) an initiator selected from either two pairs of probes hybridizable with target such that they are capable of being ligated in LCR or a pair of primers hybridizable with target so as to be capable of initiating PCR, wherein at least one of the probes or primers is modified such that, when the initiator is hybridized, a ligase or polymerase is substantially incapable of recognizing the initiator as its substrate;

(b) an assembling reagent selected from either a ligase or a polymerase enzyme for assembling an amplification product; and (c) a correcting reagent capable of correcting the modified probe/primer in a target dependent manner to render the probe/primer-template complex recognizable by the ligase or polymerase.

26. The kit of claim 25 wherein the correcting reagent comprises RNAse H.

27. The kit of claim 25 wherein the correcting reagent comprises endonuclease IV.

28. The kit of claim 25 wherein the correcting reagent comprises a mismatch repair enzyme.

29. The kit of claim 25 wherein the initiator comprises two pairs of probes, the assembling reagent comprises a ligase, and the correcting reagent comprises a polymerase.

30. The kit of claim 25 wherein the initiator comprises two pairs of probes, the assembling reagent comprises a ligase, and the correcting reagent comprises fifth and sixth probes.

31. The method of claim 14 wherein n is an integer from 1 to 5.

32. The method of claim 31 wherein m is an integer from 1 to 5.

33. The method of claim 14 wherein the dissociation of step (e) is effected by heating the reaction mixture.

34. The method of claim 33 wherein the extension of step (c) is, effected by a polymerase.

35. The method of claim 34 wherein the ligase and polymerase are stable under the conditions of dissociation.

36. The method of claim 14 wherein at least two probes are labeled with a hook moiety having a specific ligand-receptor affinity.

37. The method of claim 36 wherein the two probes bearing said hook moieties are at opposite ends of the amplification product.

38. The method of claim 37 wherein the hook moieties are different.

39. The method of claim 36 wherein all four probes are labeled with a hook moiety having a specific ligand-receptor affinity.

40. A method of detecting a target nucleic acid sequence in a sample comprising:

(a) providing four oligonucleotide probes including first and second probes hybridizable with the same strand of target, a third probe hybridized to the first probe and a fourth probe hybridized to the second probe, wherein the first probe is complementary to a first segment of the target and the second probe is complementary to a second segment of the target which is 5' of the first segment, the probes being arranged such that:

(i) the 5' end of the first segment of the target is spaced from the 3' end of the second segment by a span of $X_n$ bases, each X being independently selected from a set N consisting of from one to any three of the four bases, and n being any integer greater than or equal to 1;

(ii) when the third probe is hybridized to the first probe, there is a 5' recess in the third probe such that the base on the first probe complementary to the 5' end of the third probe is spaced from the 3' end of the first probe by a segment of $Y_m$ bases, each Y being independently selected from a set M consisting of from zero to any three of the four bases, and m being zero or any integer greater than or equal to 1, provided that at least one base remains unused in the $X_n$ and $Y_m$ gaps to comprise the set not N and not M, and that $X_n$ is not complementary to $Y_m$;

(iii) the base adjacent the 5' end of $X_n$ and the base adjacent the 5' end of $Y_m$ are selected from a set Q, which consists of not N and not M; and (iv) when the fourth probe is hybridized to the second probe there is no 3' recess in the fourth probe;

(b) treating said hybridized probes and sample nucleic acid under denaturing conditions to separate double stranded complexes into a mixture of single strands;

(c) treating said mixture of single strands under hybridizing conditions to form probe-target complexes, if target is present;

(d) extending the first probe using the $X_n$ span as template and an excess of deoxy X' triphosphates; and, if target-complement is present, extending the fourth probe using the $Y_m$ span as template and deoxy Y' triphosphates, wherein X' and Y' represent the complements of X and Y, respectively;

(e) joining the first probe to the second probe and, optionally, the third probe to the fourth probe to form a fused amplification product;

(f) denaturing the amplification product from the target and repeating the hybridization, correction and joining steps, it being understood that the fused amplification product is the equivalent of target or target-complement in subsequent repetitions, thereby to generate an amplified quantity of fused amplification product; and (g) detecting said quantity of fused amplification product, as a measure of the target sequence present in the sample.

41. The method of claim 40 wherein n is an integer from 1 to 5.

42. The method of claim 41 wherein m is an integer from 1 to 5.

43. The method of claim 41 wherein m is 0.

44. The method of claim 40 wherein the denaturation of steps (b) and (f) is effected by heating the reaction mixture.

45. The method of claim 40 wherein the extending and joining steps are performed using enzymatic reagents that are stable under the denaturation conditions.

46. The method of claim 40 wherein at least two probes are labeled with a hook moiety having a specific ligand-receptor affinity.

47. The method of claim 46 wherein the two probes bearing said hook moieties are at opposite ends of the amplification product.

48. The method of claim 47 wherein the hook moieties are different.

49. The method of claim 46 wherein all four probes are labeled with a hook moiety having a specific ligand-receptor affinity.

* * * * *

UNITED STATES PATENT AND TRADEMARK OFFICE
CERTIFICATE OF CORRECTION

PATENT NO. : 5,792,607
DATED : August 11, 1998
INVENTOR(S) : Backman et al.

Page 1 of 3

It is certified that error appears in the above-identified patent and that said Letters Patent is hereby corrected as shown below:

Column 4, line 50, change "bas e" to --base--.

Column 8, line 51, change "Jbe" to --be--.

Column 9, line 12, change " $R_{6501}$ " to --R6501--.

Column 10, line 16, change "an" to --Au--.

Column 15, line 8, change " $X_m/N$ " to -- $\mathbf{X_n/N}$ --.

Column 16, line 3, change "disthaving" to --distinguish--.

UNITED STATES PATENT AND TRADEMARK OFFICE
CERTIFICATE OF CORRECTION

PATENT NO. : 5,792,607
DATED : August 11, 1998
INVENTOR(S) : Backman et al.

Page 2 of 3

It is certified that error appears in the above-identified patent and that said Letters Patent is hereby corrected as shown below:

Column 16, line 17, change "B and ' " to --B and B'--.

Column 16, line 18, change "F and' " to --F and F'--.

Column 16, line 54, change "to the end" to --to the 3' end--.

Column 19, line 11, change "TTM" to --TTAA--.

Column 19, line 59, change "rCrCCC" to --rCrCCC--.

Column 19, line 60, change "TACrCrC" to --TACrCrC--.

Column 20, line 7, change "JG" to --JG--.

Column 20, line 10, change "GJ" to --GJ--.

Column 20, line 21, change "AC" to --AC--.

Column 20, line 22, change "CA" to --CA--.

UNITED STATES PATENT AND TRADEMARK OFFICE
CERTIFICATE OF CORRECTION

PATENT NO. : 5,792,607
DATED : August 11, 1998
INVENTOR(S) : Backman et al.

It is certified that error appears in the above-identified patent and that said Letters Patent is hereby corrected as shown below:

Column 20, line 52, change "TTM" to --TTAA--.

Column 20, line 61, change "<10 kb" to --≤10 kb--.

Column 21, line 18, change "AND" to --NAD--.

Column 21, line 21, change "A and' " to --A and B' --.

Column 21, line 22, change "B and A' " to --B and A'' --.

Column 21, line 24, change "replaced A' " to --replaced A'' --.

Column 22, line 60, change "targetbackground" to --target/background--.

Column 23, line 27, change "T(A" to --TGA--.

Column 23, line 29, change "AGC" to --ATGC--.

Column 23, line 30, change "TCT" to --TGT--.

Signed and Sealed this

Twenty-third Day of March, 1999

Attest:

Q. TODD DICKINSON

*Attesting Officer*    Acting Commissioner of Patents and Trademarks